US009993488B2

United States Patent

(12) United States Patent
Yadidi

(10) Patent No.: US 9,993,488 B2
(45) Date of Patent: Jun. 12, 2018

(54) DRY POWDER FORMULATIONS FOR INHALATION

(71) Applicant: OtiTopic Inc., Los Angeles, CA (US)

(72) Inventor: Kambiz Yadidi, Los Angeles, CA (US)

(73) Assignee: OTITOPIC INC., Los Angeles, CA (US)

( * ) Notice: Subject to any disclaimer, the term of this patent is extended or adjusted under 35 U.S.C. 154(b) by 0 days. days.

(21) Appl. No.: 14/628,148

(22) Filed: Feb. 20, 2015

(65) Prior Publication Data

US 2016/0022705 A1 Jan. 28, 2016

Related U.S. Application Data

(60) Provisional application No. 61/942,545, filed on Feb. 20, 2014, provisional application No. 62/031,811, filed on Jul. 31, 2014.

(51) Int. Cl.

| | |
|---|---|
| *A61K 31/616* | (2006.01) |
| *A61K 31/4365* | (2006.01) |
| *A61K 9/00* | (2006.01) |
| *A61K 9/16* | (2006.01) |

(52) U.S. Cl.
CPC .......... *A61K 31/616* (2013.01); *A61K 9/0075* (2013.01); *A61K 9/1617* (2013.01); *A61K 31/4365* (2013.01)

(58) Field of Classification Search
CPC .............. A61K 31/616; A61K 31/4365; A61K 9/0075; A61K 9/1617
See application file for complete search history.

(56) References Cited

U.S. PATENT DOCUMENTS

| | | | |
|---|---|---|---|
| 3,906,950 | A | 9/1975 | Cocozza |
| 4,069,819 | A | 1/1978 | Valentini et al. |
| 4,353,365 | A | 10/1982 | Hallworth et al. |
| 4,885,287 | A | 12/1989 | Hussain et al. |
| 4,995,385 | A | 2/1991 | Valentini et al. |
| 5,327,883 | A | 7/1994 | Williams et al. |
| 5,506,203 | A | 4/1996 | Backstrom et al. |
| 5,511,416 | A | 4/1996 | Shambayati et al. |
| 5,511,726 | A | 4/1996 | Greenspan et al. |
| 5,518,998 | A | 5/1996 | Backstrom et al. |
| 5,639,441 | A | 6/1997 | Sievers et al. |
| 5,673,686 | A | 10/1997 | Villax et al. |

(Continued)

FOREIGN PATENT DOCUMENTS

| | | | |
|---|---|---|---|
| EP | 1177805 | A1 | 2/2002 |
| EP | 1238680 | A1 | 9/2002 |

(Continued)

OTHER PUBLICATIONS

"Aspirin", Martindale: The Complete Drug Reference, 33rd ed., 2002 Pharmaceutical press, pp. 14-18.

(Continued)

*Primary Examiner* — Trevor Love
(74) *Attorney, Agent, or Firm* — FisherBroyles, LLP; James W. Hill

(57) ABSTRACT

A respirable dry powder including acetylsalicylic acid in particles having a mass median aerodynamic diameter (MMAD) within a range of about 0.5 μm to about 10 μm. The respirable dry powder may contain a pharmaceutically acceptable excipient, such as a phospholipid, in an amount ranging from about 0.1% (w/w) to about 10% (w/w) of the particles.

14 Claims, 8 Drawing Sheets

(56) References Cited

U.S. PATENT DOCUMENTS

| | | |
|---|---|---|
| 5,724,957 A | 3/1998 | Rubsamen et al. |
| 5,750,559 A | 5/1998 | Bianco |
| 5,855,913 A | 1/1999 | Hanes et al. |
| 5,874,064 A | 2/1999 | Edwards et al. |
| 5,875,776 A | 3/1999 | Vaghefi |
| 5,993,805 A | 11/1999 | Sutton et al. |
| 6,051,256 A | 4/2000 | Platz et al. |
| 6,098,620 A | 8/2000 | Lloyd et al. |
| 6,131,570 A | 10/2000 | Flaim et al. |
| 6,136,295 A | 10/2000 | Edwards et al. |
| 6,136,346 A | 10/2000 | Eljamal et al. |
| 6,187,344 B1 | 2/2001 | Eljamal et al. |
| 6,254,854 B1 | 7/2001 | Edwards et al. |
| 6,284,282 B1 | 9/2001 | Maa et al. |
| 6,309,623 B1 | 10/2001 | Weers et al. |
| 6,358,530 B1 | 3/2002 | Eljamal et al. |
| 6,408,846 B1 | 6/2002 | Ohki et al. |
| 6,423,344 B1 | 7/2002 | Platz et al. |
| 6,455,028 B1 | 9/2002 | Wulffhart et al. |
| 6,503,480 B1 | 1/2003 | Edwards et al. |
| 6,546,928 B1 | 4/2003 | Herman et al. |
| 6,561,186 B2 | 5/2003 | Casper et al. |
| 6,565,885 B1 | 5/2003 | Tarara et al. |
| 6,569,406 B2 | 5/2003 | Stevenson et al. |
| 6,582,729 B1 | 6/2003 | Eljamal et al. |
| 6,592,904 B2 | 7/2003 | Platz et al. |
| 6,630,169 B1 | 10/2003 | Bot et al. |
| 6,638,495 B2 | 10/2003 | Weers et al. |
| 6,652,837 B1 | 11/2003 | Edwards et al. |
| 6,705,313 B2 | 3/2004 | Niccolai |
| 6,732,732 B2 | 5/2004 | Edwards et al. |
| 6,737,042 B2 | 5/2004 | Rabinowitz et al. |
| 6,737,044 B1 | 5/2004 | Dickinson et al. |
| 6,766,799 B2 | 7/2004 | Edwards et al. |
| 6,848,197 B2 | 2/2005 | Chen et al. |
| 6,880,555 B1 | 4/2005 | Brunnberg et al. |
| 6,881,398 B2 | 4/2005 | Myrman et al. |
| 6,893,657 B2 | 5/2005 | Roser et al. |
| 6,921,527 B2 | 7/2005 | Patton et al. |
| 6,979,437 B2 | 12/2005 | Bartus et al. |
| 6,994,842 B2 | 2/2006 | Lee et al. |
| 6,998,137 B2 | 2/2006 | Shih et al. |
| 7,146,978 B2 | 12/2006 | Edwards et al. |
| 7,182,961 B2 | 2/2007 | Batycky et al. |
| 7,201,929 B1 | 4/2007 | Finkelstein |
| 7,205,343 B2 | 4/2007 | Dellamary et al. |
| 7,267,813 B2 | 9/2007 | Watanabe et al. |
| 7,278,425 B2 | 10/2007 | Edwards et al. |
| 7,284,553 B2 | 10/2007 | Hochrainer |
| 7,306,787 B2 | 12/2007 | Tarara et al. |
| 7,431,916 B2 | 10/2008 | Nilsson et al. |
| 7,516,741 B2 | 4/2009 | Glusker et al. |
| 7,521,068 B2 | 4/2009 | Bosch et al. |
| 7,541,022 B2 | 6/2009 | Staniforth et al. |
| 7,556,035 B2 | 7/2009 | Young et al. |
| 7,556,798 B2 | 7/2009 | Edwards et al. |
| 7,559,325 B2 | 7/2009 | Dunkley et al. |
| 7,601,336 B2 | 10/2009 | Lewis et al. |
| 7,628,978 B2 | 12/2009 | Weers et al. |
| 7,669,596 B2 | 3/2010 | Alston |
| 7,744,855 B2 | 6/2010 | Staniforth et al. |
| 7,790,145 B2 | 9/2010 | Weers et al. |
| 7,806,117 B2 | 10/2010 | Tsutsui |
| 7,878,193 B2 | 2/2011 | Kladders et al. |
| 7,919,119 B2 | 4/2011 | Straub et al. |
| 7,954,491 B2 | 6/2011 | Hrkach |
| 8,069,851 B2 | 12/2011 | Dunkley et al. |
| 8,075,919 B2 | 12/2011 | Brown et al. |
| 8,114,438 B2 | 2/2012 | Pipkin et al. |
| 8,168,223 B1 | 5/2012 | Tarara et al. |
| 8,173,168 B2 | 5/2012 | Platz et al. |
| 8,201,555 B2 | 6/2012 | Chawla |
| 8,246,934 B2 | 8/2012 | Weers et al. |
| 8,614,255 B2 | 12/2013 | Blizzard et al. |
| 2002/0025917 A1 | 2/2002 | Pappalardo |
| 2003/0186843 A1 | 10/2003 | Staniforth et al. |
| 2004/0206350 A1 | 10/2004 | Alston et al. |
| 2005/0000518 A1 | 1/2005 | Dunkley et al. |
| 2005/0084528 A1 | 4/2005 | Saeed et al. |
| 2005/0180926 A1 | 8/2005 | Lecourt et al. |
| 2006/0249144 A1 | 11/2006 | DeHaan et al. |
| 2006/0293273 A1 | 12/2006 | Mangano et al. |
| 2007/0021382 A1 | 1/2007 | Assaf et al. |
| 2008/0044481 A1 | 2/2008 | Harel et al. |
| 2008/0066741 A1 | 3/2008 | LeMahieu et al. |
| 2008/0127972 A1 | 6/2008 | Morton et al. |
| 2008/0226736 A1 | 9/2008 | Caponetti et al. |
| 2008/0306033 A1 | 12/2008 | Franzone et al. |
| 2009/0208582 A1 | 8/2009 | Johnston et al. |
| 2009/0308392 A1 | 12/2009 | Smutney et al. |
| 2010/0132705 A1 | 6/2010 | De Vos |
| 2010/0234442 A1 | 9/2010 | Duarte-Vazquez et al. |
| 2010/0242960 A1 | 9/2010 | Zangerle |
| 2010/0258118 A1 | 10/2010 | Morton |
| 2010/0316724 A1 | 12/2010 | Whitfield et al. |
| 2010/0319694 A1 | 12/2010 | Cook et al. |
| 2011/0277752 A1 | 11/2011 | Cheu et al. |
| 2012/0132203 A1 | 5/2012 | Hodson et al. |
| 2012/0145150 A1 | 6/2012 | Donovan et al. |
| 2012/0152245 A1 | 6/2012 | Rolfs et al. |
| 2012/0291780 A1 | 11/2012 | Donovan et al. |
| 2014/0065219 A1 | 3/2014 | Bosch et al. |
| 2014/0174437 A1 | 6/2014 | Yadidi |
| 2014/0174440 A1 | 6/2014 | Yadidi |
| 2014/0322328 A1 | 10/2014 | Yadidi et al. |
| 2014/0326812 A1 | 11/2014 | Dodd et al. |

FOREIGN PATENT DOCUMENTS

| | | |
|---|---|---|
| EP | 1350511 A1 | 10/2003 |
| EP | 1814521 A1 | 8/2007 |
| WO | 9916419 A1 | 4/1999 |
| WO | 0000215 A1 | 1/2000 |
| WO | 2000000176 | 1/2000 |
| WO | WO-2000/027359 A1 | 5/2000 |
| WO | WO-2009/089822 A2 | 7/2009 |
| WO | WO-2012/061902 A1 | 5/2012 |
| WO | 2012107765 A2 | 8/2012 |

OTHER PUBLICATIONS

"Internal Analgesic: Antipyretic, and Antirheumatic Drug Products for Over-The-Counter Human Use: Final Rule for Professional Labeling of Aspirin, Buffered Aspirin, and Aspirin in Combination with Antacid Drug Products," Federal Register, Oct. 23, 1998, vol. 63, No. 205, pp. 56802-56819.

"Physicians' Health Study I," <http://phs.bwh.harvard.edu/phs1.htm>, Mar. 2009.

Algra, et al., "Aspirin at Any Dose Above 30 mg Offers Only Modest Protection After Cerebral Ischemia," J of Neurology, Neurosurgery & Psychiatry, 1996, 60:197-199.

Aspirin Dosage-Drugs, www.drugs.com, Dec. 2011.

ATT Collaboration, "Aspirin in the Primary and Secondary Prevention of Vascular Disease: Collaborative Meta-Analysis of Individual Participant Data from Randomised Trials," The Lancet, 2009, 373:1849-1860.

Awa, et al., "Prediction of time-dependent interaction of aspirin with ibuprofen using a pharmacokinetic/pharmacodynamics model," Journal of Clinical Pharmacy and Therapeutics, 2012, vol. 37, pp. 469-474.

Boysen, et al., "Danish Very-low-dose Aspirin After Carotid Endarterectomy Trial," Stroke, 1988, 19:1211-1215.

Chew, et al., "The Role of Particle Properties in Pharmaceutical Powder Inhalation Formulations," Journal of Aerosol Medicine, 2002, vol. 15, No. 3, pp. 325-330.

Christen, et al., "Low-dose Aspirin and Risk of Cataract and Subtypes in a Randomized Trial of U.S. Physicians" Ophthalmic Epidemiology, 1998, vol. 5, No. 3, pp. 133-142.

Fehri, et al., "Bioavailability of Acetylsalicylic Acid Administered Orally or Rectally in the Rabbit," J. Pharma Belg, 1989, vol. 44, No. 1, pp. 5-10.

(56) References Cited

OTHER PUBLICATIONS

Geller, et al., "Development of an Inhaled Dry-Powder Formulation of Tobramycin Using PlumoSphere Technology," J Aerosol Med Pulm Drug Deliv, Aug. 2011, 24(4), pp. 175-182.
Hadinoto et al., "Drug release study of large hollow nanoparticulate aggregates carrier particles for pulmonary delivery," International Journal of Pharmaceutics 341 (2007) 195-206.
Hadinoto, et al., "Dry powder aerosol delivery of large hollow nanoparticulate aggregates as prospective carriers of nanoparticulate drugs: Effects of phospholipids," International Journal of Pharmaceuticals, Oct. 2006, 33: 187-198.
Hovione—Particle Design Technologies, <http://www.hovione.com/pd/particledesigntechnologies.asp>, visited Aug. 2013.
Hovione TwinCaps Dry Powder Inhaler, <http://www.hovione.com/twincaps/twincaps.asp>, visited Aug. 2013.
Iwamoto, "Gastrointestinal and Hepatic First-Pass Metabolism of Aspirin in Rats," J Pharm Pharmacol. Mar. 1982; 34(3), pp. 176-180.
Jaffe, et al., "Recovery of Endothelial Cell Prostacyclin Production after Inhibition by Low Doses of Aspirin," The American Society for Clinical Investigation, Inc., Mar. 1979, vol. 63, pp. 532-535.
Kim, et al., "Airway Responsiveness to Inhaled Aspirin is Influenced by Airway Hyperresponsiveness in Asthmatic Patients," Korean J Intern Med, Sep. 2010; 25(3): 309-316.
Kurth, et al., "Inhibition of Clinical Benefits of Aspirin on First Myocardial Infarction by Nonsteroidal Antiinflammatory Drugs," Circulation, 2003, 108:1191-1195.
Phillips et al., "Inhaled lysine-aspirin as a bronchoprovocation procedure in aspirin-sensitive asthma: its repeatability, absence of a late-phase reaction, and the role of histamine," J Allergy Clin Immunol, Aug. 1989; 84(2):232-41.
Press release by Activaero GmbH, Dec. 19, 2006, <http://www.pharmaloco.com/news_detail/Activaero+and+Group+of+Resaerchers+Receive+Grant+for+Develop/14009/index.html>.
Rocca, et al., "Variability in the Responsiveness to Low-Dose Aspirin: Pharmacological and Disease-Related Mechanisms," Thrombosis, 2012, 11 pages.
Roth, et al., "Aspirin, Platelets, and Thrombosis: Theory and Practice," Blood, Feb. 15, 1994, vol. 83, No. 4, pp. 885-898.
Sestini et al., "Different Effects of Inhaled Aspirin-like Drugs on Allergen-Induced Early and Late Asthmatic Responses," Am J Respir Crit Care Med, Apr. 1, 1999 vol. 159 No. 4 1228-1233.
Sestini, et al., "Protective effect of inhaled lysine acetylsalicylate on allergen-induced early and late asthmatic reactions," J Allergy Clin Immunol, 1997 vol. 100, pp. 71-77.
Soleti et al., "Aspirin inhalation treatment for COPD patients: Preliminary studies on PK and inflammatory biomarkers," Thematic Poster Session, P825, Drug delivery and pharmacokinetics I, Sep. 25, 2011, p. 138s.

Sung, et al., "Nanoparticles for Drug Delivery to the Lungs," Trends in Biotechnology, 2007, vol. 25, No. 12.
The Dutch TIA Trial Study Group, "A Comparison of Two Doses of Aspirin (30 mg vs. 283 mg a day) in Patients After a Transient Ischemic Attack or Minor Ischemic Stroke," The New England Journal of Medicine, 1991, vol. 325, No. 18, pp. 1261-1266.
EPO, "Extended European Search Report" for EP Application No. 15827152.8, dated Jan. 10, 2018, dated Jan. 10, 2018, 8 pgs.
USPTO, "International Search Report" for PCT Application No. PCT/US15/16969, dated May 20, 2015, 2 pgs.
USPTO, "International Search Report" for PCT Application No. PCT/US15/43128, dated Nov. 2, 2015, 2 pgs.
Bode-Boger SM et al., "Effects of very low dose and enteric-coated acetylsalicylic acid on prostacyclin and thromboxane formation and on bleeding time in healthy subjects", Eur J Clin Pharmacol., 54, 707-14, 1998.
Byron PR, "Prediction of drug residence times in regions of the human respiratory tract following aerosol inhalation", J. Pharm. Sci. 75, 433-438, 1986.
Clarke et al., "The relationship between powder inhaler resistance and peak inspiratory conditions in healthy volunteers—implications for in vitro testing," J Aerosol Med 6, 99-110, 1993.
Dalby et al., "Comparison of output particle size distribution from pressurized aerosols formulated as solutions or suspensions," Pharm Res 5, 36-39, 1988.
DeHaan et al., "Predicting extrathoracic deposition from dry powder inhalers," J Aerosol Science 35, 309-331, 2004.
Dressman et al., "Biowaiver Monograph for Immediate-Release Solid Oral Dosage Forms: Acetylsalicylic Acid", J Pharm Sci. 101(8):2653-67, Aug. 2012.
Gonda I, "Aerosols for delivery of therapeutic and diagnostic agents to the respiratory tract", Critical Reviews in Therapeutic Drug Carrier Systems 6, 273-313, 1990.
Heyder J. et al., "Deposition of particles in the human respiratory tract in the size range 0.005-15 µm", J. Aerosol Sci. 17, 811-825, 1986.
Hoet, Peter et al., "Nanoparticles—known and unknown health risks", J. Nanobiotechnol 2, 1477-3155, 2004.
Leone-Bay, Andrea et al., "Technosphere Technology: A platform for inhaled protein therapeutics", Ondrugdelivery, Pulmonary Delivery: Innovative Technologies Breathing New Life into Inhalable Therapeutics, 2006, pp. 8-11, available at http://www.ondrugdelivery.com/publications/Pulmonary.pdf.
Li et al., "Aspirin particle formation by electric-field-assisted release of droplets," Chemical Engineering Science 61, 3091-3097, 2006.
Maree,et al. "Platelet Response to Low-Dose Enteric-Coated Aspirin in Patients With Stable Cardiovascular Disease", J Am Coll Cardiol, 47, 1258-63, 2005.
Tiddens et al., "Effect of dry powder inhaler resistance on the inspiratory flow rates and volumes of cystic fibrosis patients of six years and older," Journal of Aerosol Med. 19, 456-465, 2006.
European Patent Office, Extended European Search Report for EP15752250.9, dated Sep. 19, 2017, 7 pages.

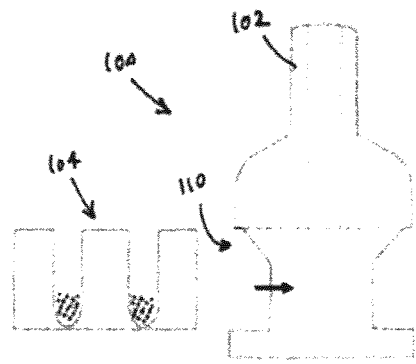
FIG. 2A
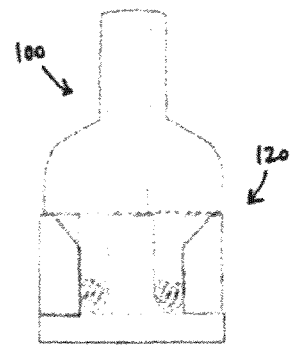
FIG. 2B
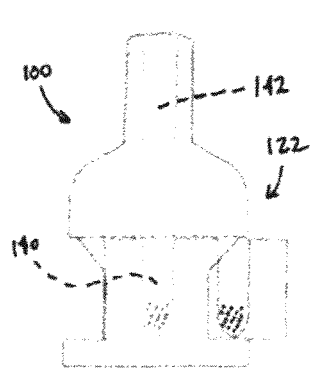
FIG. 2C
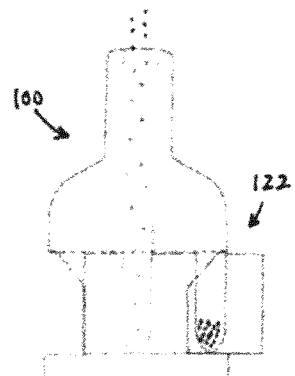
FIG. 2D
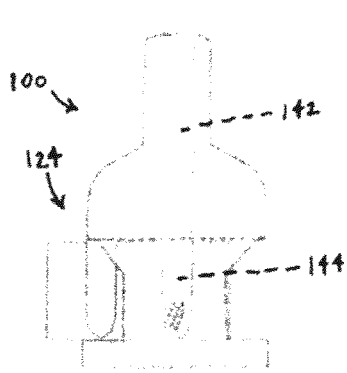
FIG. 2E
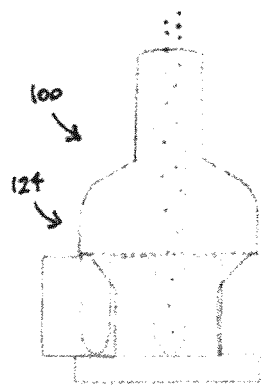
FIG. 2F
Figure 2

DRY POWDER FORMULATIONS FOR INHALATION

RELATED APPLICATIONS

This application claims priority to U.S. Provisional Application No. 61/942,545, entitled "DRY POWDER FORMULATIONS FOR INHALATION," filed on Feb. 20, 2014, and U.S. Provisional Application No. 62/031,811, entitled, "DRY POWDER FORMULATIONS FOR INHALATION," filed on Jul. 31, 2014, which is incorporated herein by reference in their entirety.

FIELD

The subject technology relates generally to pulmonary delivery of NSAIDs, such as aspirin. The subject technology also relates generally to apparatuses and methods for delivery of substances, e.g., medication, to the lungs by inhalation for treating disease.

BACKGROUND

Pulmonary delivery of therapeutic agents can offer several advantages over other modes of delivery. These advantages include rapid onset, the convenience of patient self-administration, the potential for reduced drug side-effects, ease of delivery by inhalation, the elimination of needles, and the like. Inhalation therapy is capable of providing a drug delivery system that is easy to use in an inpatient or outpatient setting, results in very rapid onset of drug action, and produces minimal side effects.

Metered dose inhalers (MDIs) are used to deliver therapeutic agents to the respiratory tract. MDIs are generally suitable for administering therapeutic agents that can be formulated as solid respirable dry particles in a volatile liquid under pressure. Opening of a valve releases the suspension at relatively high velocity. The liquid then volatilizes, leaving behind a fast-moving aerosol of dry particles that contain the therapeutic agent.

Liquid aerosol delivery is one of the oldest forms of pulmonary drug delivery. Typically, liquid aerosols are created by an air jet nebulizer, which releases compressed air from a small orifice at high velocity, resulting in low pressure at the exit region due to the Bernoulli effect. See, e.g., U.S. Pat. No. 5,511,726. The low pressure is used to draw the fluid to be aerosolized out of a second tube. This fluid breaks into small droplets as it accelerates in the air stream. Disadvantages of this standard nebulizer design include relatively large primary liquid aerosol droplet size often requiring impaction of the primary droplet onto a baffle to generate secondary splash droplets of respirable sizes, lack of liquid aerosol droplet size uniformity, significant recirculation of the bulk drug solution, and low densities of small respirable liquid aerosol droplets in the inhaled air. In addition, a particular compound of interest may not be compatible with solvents typically used in nebulizer delivery systems.

Ultrasonic nebulizers use flat or concave piezoelectric disks submerged below a liquid reservoir to resonate the surface of the liquid reservoir, forming a liquid cone which sheds aerosol particles from its surface (U.S. 2006/0249144 and U.S. Pat. No. 5,551,416). Since no airflow is required in the aerosolization process, high aerosol concentrations can be achieved, however the piezoelectric components are relatively expensive to produce and are inefficient at aerosolizing suspensions, requiring active drug to be dissolved at low concentrations in water or saline solutions. Newer liquid aerosol technologies involve generating smaller and more uniform liquid respirable dry particles by passing the liquid to be aerosolized through micron-sized holes. See, e.g., U.S. Pat. No. 6,131,570; U.S. Pat. No. 5,724,957; and U.S. Pat. No. 6,098,620. Disadvantages of this technique include relatively expensive piezoelectric and fine mesh components as well as fouling of the holes from residual salts and from solid suspensions.

Dry powder inhalation has historically relied on lactose blending to allow for the dosing of particles that are small enough to be inhaled, but aren't dispersible enough on their own. This process is known to be inefficient and to not work for some drugs. Several groups have tried to improve on these shortcomings by developing dry powder inhaler (DPI) formulations that are respirable and dispersible and thus do not require lactose blending. Dry powder formulations for inhalation therapy are described in U.S. Pat. No. 5,993,805 to Sutton et al.; U.S. Pat. No. 69,216,527 to Platz et al.; WO 0000176 to Robinson et al.; WO 9916419 to Tarara et al.; WO 0000215 to Bot et al; U.S. Pat. No. 5,855,913 to Hanes et al.; and U.S. Pat. Nos. 6,136,295 and 5,874,064 to Edwards et al.

Broad clinical application of dry powder inhalation delivery has been limited by difficulties in generating dry powders of appropriate particle size, particle density, and dispersibility, in keeping the dry powder stored in a dry state, and in developing a convenient, hand-held device that effectively disperses the respirable dry particles to be inhaled in air. In addition, the particle size of dry powders for inhalation delivery is inherently limited by the fact that smaller respirable dry particles are harder to disperse in air. Dry powder formulations, while offering advantages over cumbersome liquid dosage forms and propellant-driven formulations, are prone to aggregation and low flowability, which considerably diminish dispersibility and the efficiency of dry powder-based inhalation therapies. For example, interparticular Van der Waals interactions and capillary condensation effects are known to contribute to aggregation of dry particles. Hickey, A. et al., "Factors Influencing the Dispersion of Dry Powders as Aerosols", Pharmaceutical Technology, August, 1994.

To overcome interparticle adhesive forces, Batycky et al. in U.S. Pat. No. 7,182,961 teach production of so called "aerodynamically light respirable particles," which have a volume median geometric diameter (VMGD) of greater than 5 microns ($\mu$m) as measured using a laser diffraction instrument such as HELOS (manufactured by Sympatec, Princeton, N.J.). See Batycky et al., column 7, lines 42-65. Another approach to improve dispersibility of respirable particles of average particle size of less than 10 $\mu$m, involves the addition of a water soluble polypeptide or addition of suitable excipients (including amino acid excipients such as leucine) in an amount of 50% to 99.9% by weight of the total composition. Eljamal et al., U.S. Pat. No. 6,582,729, column 4, lines 12-19 and column 5, line 55 to column 6, line 31. However, this approach reduces the amount of active agent that can be delivered using a fixed amount of powder. Therefore, an increased amount of dry powder is required to achieve the intended therapeutic results, for example, multiple inhalations and/or frequent administration may be required. Still other approaches involve the use of devices that apply mechanical forces, such as pressure from compressed gasses, to the small particles to disrupt interparticular adhesion during or just prior to administration. See, e.g., U.S. Pat. No. 7,601,336 to Lewis et al., U.S. Pat. No.

6,737,044 to Dickinson et al., U.S. Pat. No. 6,546,928 to Ashurst et al., or U.S. Pat. Applications 20090208582 to Johnston et al.

A further limitation that is shared by each of the above methods is that the aerosols produced typically include substantial quantities of inert carriers, solvents, emulsifiers, propellants, and other non-drug material. In general, the large quantities of non-drug material are required for effective formation of respirable dry particles small enough for alveolar delivery (e.g. less than 5 µm and preferably less than 3 μm). However, these amounts of non-drug material also serve to reduce the purity and amount of active drug substance that can be delivered. Thus, these methods remain substantially incapable of introducing large active drug dosages accurately to a patient for systemic delivery.

A thromboembolic event, such as myocardial infarction, deep venous thrombosis, pulmonary embolism, thrombotic stroke, etc., can present with certain symptoms that allow a patient or clinician to provide an initial therapy or treatment for the event. In some situations, an 81 mg, low dose, or baby aspirin or a regular aspirin (330 mg) may be orally administered in order to provide an initial treatment for the patient. In some cases, it has been recommended that upon first experiencing symptoms suspected of being due to a coronary event, patients are to chew and swallow two low dose aspirin tablets, a total dose of about 162 mg of aspirin.

There remains a need for providing novel formulations of non-steroidal anti-inflammatory drugs ("NSAIDs"), such as aspirin, that are suitable for pulmonary delivery.

SUMMARY

The subject technology generally relates to respirable dry powders comprising dry particles that comprise an NSAID, such as acetylsalicylic acid, as an active ingredient. The respirable dry particles may be large or small, e.g., a geometric diameter (VMGD) between 0.5 μm and 30 μm. Alternatively or in addition, the respirable dry powders can have a mass median aerodynamic diameter (MMAD) of about 20 μm or less. Optionally, the MMAD of the particles may be between 0.5 and 10 μm, more preferably between 1 and 10 μm, even more preferably having a size distribution where 90% of the formulation comprises particles having an MMAD of about 6 μm or less, 50% of the formulation comprises particles having an MMAD of about 3 μm or less, and 10% of the formulation comprises particles having an MMAD of about 1 μm or less.

The dry powders may also comprise a mixture of particles of large sizes (e.g., 20-30 μm) and of small sizes (e.g., 5 μm or less). This way, smaller particles could reach the lower respiratory tract and larger particles would be captured in the upper respiratory tract.

The respirable dry powder compositions can include a pharmaceutically acceptable excipient, such as leucine, sodium citrate, maltodextrin, or mannitol, which may be present in an amount of about 5% to about 90% or by weight. The inclusion of an excipient is optional.

In some embodiments, the NSAID, such as acetylsalicylic acid, is provided in a dry powder formulation comprising a mixture of particles of various sizes, for example, a mixture of (i) particles having a mean geometric diameter (VMGD) and/or mass median aerodynamic diameter (MMAD) of about 5 μm or less, and (ii) particles having a mean geometric diameter (VMGD) and/or mass median aerodynamic diameter (MMAD) of 15 μm or greater. In some embodiments the composition may further include a pharmaceutically acceptable excipient. In other embodiments, the composition is free or substantially free of excipient. In certain embodiments, the composition is free or substantially free of anti-aggregation excipient.

The subject technology also relates to a respirable dry powder or dry particle, as described herein, for use in therapy (e.g., treatment, prophylaxis, or diagnosis). The subject technology also relates to the use of a respirable dry particle or dry powder, as described herein, for use in treatment (including prophylactic treatment, such as prevention or reducing the risk) of a cardiovascular disease (such as thrombosis) as described herein, and in the manufacture of a medicament for the treatment, prophylaxis or diagnosis of a cardiovascular disease (such as thrombosis) as described herein.

The subject technology also provides a drug delivery system for treating (including prophylactic treatment or reducing the risk of) a cardiovascular disease (such as thrombosis), the system comprising: a therapeutically effective dose of an NSAID (such as acetylsalicylic acid) in dry powder form; a dry powder inhaler, the dry powder inhaler comprising a mouthpiece, a reservoir for receiving the dose of the NSAID (such as acetylsalicylic acid), and an actuation member for making available the dose of the acetylsalicylic acid for inhalation by the patient through the mouthpiece. Preferably, a single inhaled dose of the NSAID (such as acetylsalicylic acid) is about 40 mg or less, more preferably, 30 mg or less. In particular, it is expected that a dosing regime using inhalable aspirin will be able to deliver pharmaceutically equivalent levels of aspirin to the patient more quickly than is possible by oral dosing.

Another aspect of at least one embodiment disclosed herein includes the recognition of a need for improved apparatuses and methods for delivery of drugs for treating disease that utilize a dosage that is effective to reduce a risk of a thromboembolic event in a patient, lower than traditional dosages, and administered using a more direct delivery mechanism to the systemic blood stream.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 1 is a schematic view of a patient using a dry powder inhaler, in accordance with some implementations of the methods and systems disclosed herein.

FIGS. 2A, 2B, 2C, 2D, 2E, and 2F illustrate usages and a configuration of a dry powder inhaler, according to some embodiments. FIGS. 2A-2F illustrate a DPI delivery device 100 having a mouthpiece 102 and a drug compartment 104. The drug compartment 104 can be inserted into an inhaler body cavity 110. FIG. 2B, the drug compartment 104 can be inserted into the body cavity 110 into a stowed position 120 for storage purposes. The drug compartment 104 can be moved to a first position 122, shown in FIG. 2C, in which a first receptacle 140 of the drug compartment 104 is aligned with a mouthpiece airway 142. In this first position 122, the drug contained in the first receptacle 140 can be delivered through the mouthpiece airway 142 to be inhaled by the patient, as illustrated in FIG. 2D. As shown in FIG. 2E, the drug compartment 104 can be moved to a second position 124 in which a second receptacle 144 is aligned with the mouthpiece airway 142. In this position, the drug contained in the second receptacle 144 can be inhaled by the patient, as illustrated in FIG. 2F.

Figure 7A:
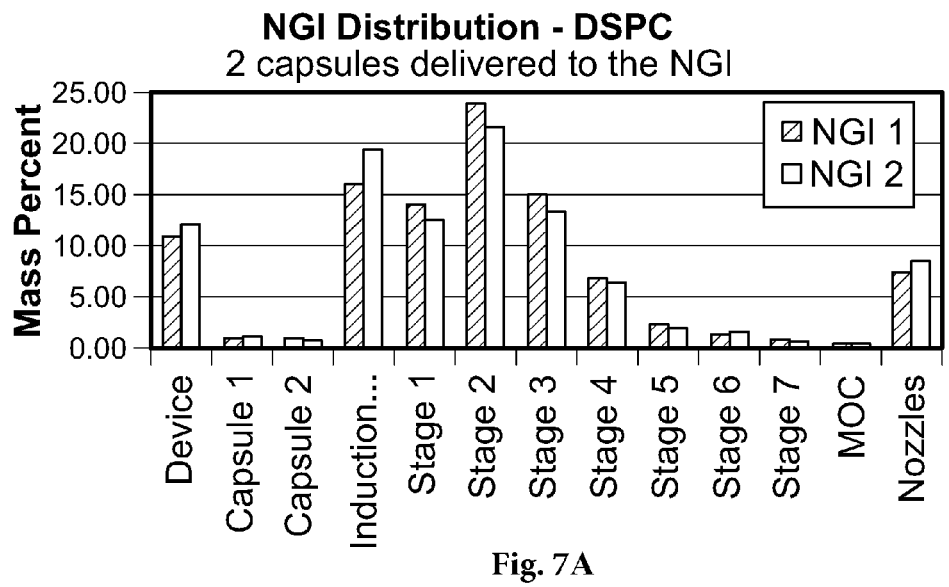
Figure 7B:
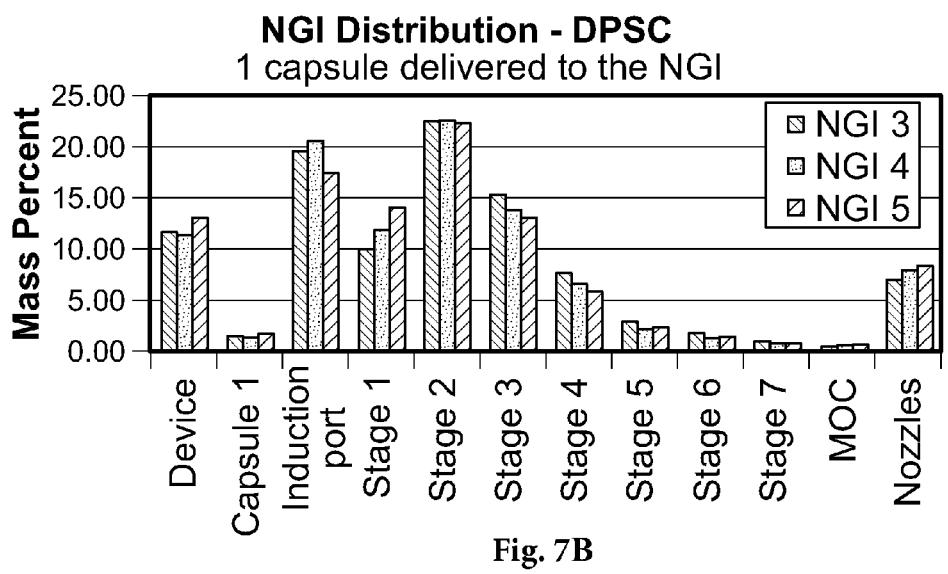

FIGS. 7A and 7B show the particle size distribution of spray-dried DSPC/aspirin particles based on NGI analysis. FIG. 7A: 2 capsules were delivered to the NGI; FIG. 7B: 1 capsule was delivered to the NGI.

Figure 8A:
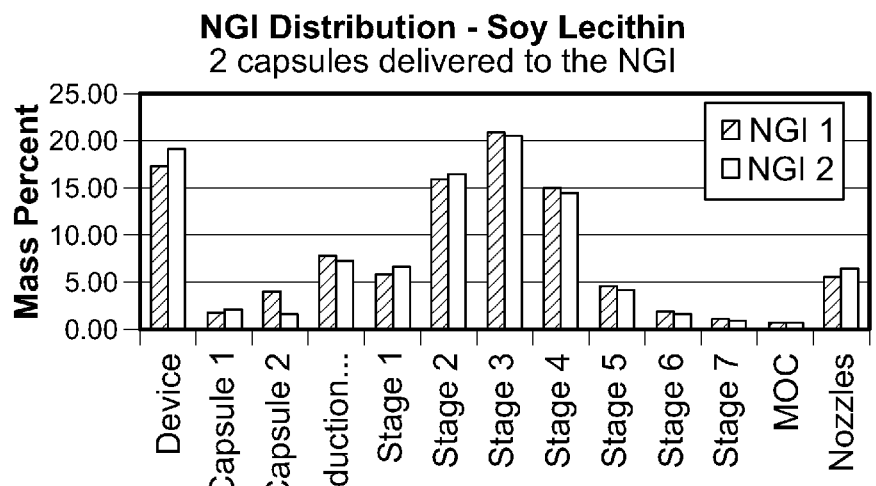
Figure 8B:
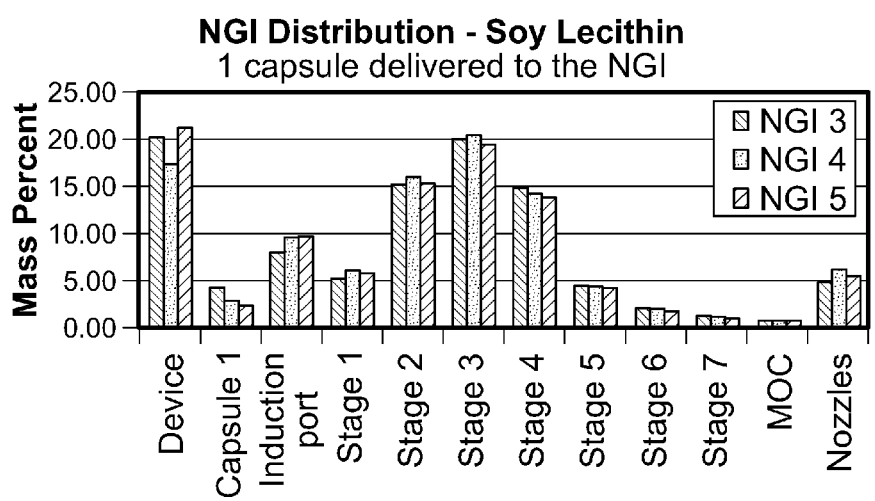

FIGS. 8A and 8B show the particle size distribution of spray-dried soy lecithin/aspirin particles based on NGI analysis. FIG. 8A: 2 capsules were delivered to the NGI; FIG. 8B: 1 capsule was delivered to the NGI.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

1. INTRODUCTION

Thromboembolic Symptoms and Events

A thromboembolic event, such as myocardial infarction, deep venous thrombosis, pulmonary embolism, thrombotic stroke, etc., can present with certain symptoms that allow a patient or clinician to provide an initial therapy or treatment for the event. In some situations, an 81 mg, low dose, or baby aspirin or a regular aspirin (330 mg) may be orally administered in order to provide an initial treatment for the patient.

According to some embodiments disclosed herein is the realization that this treatment may not act as quickly as necessary to provide a sufficient therapeutic effect and therefore, may lead to a less preferred outcome. Thus, in some embodiments, a drug delivery system and related methods are disclosed that provide an accelerated and more efficient pathway and treatment for reducing the risk of a thromboembolic event and/or providing treatment for a thromboembolic event. For example, some embodiments provide systems and methods of administering a non-steroidal anti-inflammatory drug ("NSAID") by inhalation, such as by a dry powder inhaler ("DPI") or a metered dose inhaler ("MDI").

Delivery Mechanisms for Drugs

Drugs can be administered orally in different ways, such as liquids, capsules, tablets, or chewable tablets. The oral route is used most often because it is the most convenient, safest, and least expensive. However, oral drug delivery has limitations because of the way a drug typically moves through the digestive tract.

For example, when a drug is administered orally, it is absorbed in the mouth, stomach, and the small intestine. Before the drug enters the bloodstream, it must pass through the intestinal wall and travels to the liver. While passing through the intestinal wall and liver, the drug is metabolized, which can decrease the amount of the drug that actually reaches the bloodstream. The metabolism of the drug reduces the bioavailability of the drug and is often termed the "first pass effect." The fraction of the drug lost due to the first pass effect is generally determined by absorption in the liver and gut wall, and gastrointestinal lumen enzymes, gut wall enzymes, bacterial enzymes, and hepatic (liver) enzymes.

Generally, the first pass effect on aspirin significantly reduces the bioavailability of the administered dosage. For example, due to the acidic conditions in the stomach, aspirin is absorbed in the stomach and the upper small intestine. After being absorbed, aspirin is metabolized to acetic acid and salicylate. When taken orally, generally only about one to two-thirds of the dose of aspirin is bioavailable due to the first pass effect.

Applicant has determined that even drugs that are administered by inhalation undergo a first pass effect. For drug administration by inhalation, smaller particles proceed via a nasal route, down the windpipe (trachea) and into the lungs. The size of the particles can be determinative of the overall efficacy of the treatment. Once inside the lungs, these particles are absorbed into the bloodstream. However, in the fraction of the drug that reaches the alveolar spaces of the lung, the active pharmaceutical ingredient (e.g., aspirin) will be absorbed within the capillaries and delivered to the pulmonary circulation. This material will initially circulate via the pulmonary vein back to the heart with oxygenated blood, and will then be distributed systemically via output from the left ventricle. As such, upon inhalation of the pharmaceutical, a substantial portion will avoid the first pass effect due to processing in the liver, with the result that levels of aspirin in the region of the heart will be higher than would be possible following prior art methods of oral administration.

Few drugs are administered by inhalation because the dosage of an inhaled drug, as well as the delivery timing, can often be difficult to measure. Usually, this method is used to administer drugs that act specifically on the lungs, such as aerosolized anti-asthmatic drugs in metered-dose containers, and to administer gases used for general anesthesia. In this case, the inventors have determined that it is possible to reproducibly deliver predictable doses of aspirin via a dry powder device. For example, about 85%, about 90%, about 95%, about 96%, about 97%, about 98%, or about 99% of the aspirin loaded into a dry powder inhaler can be reproducibly delivered from the inhaler device to the patient.

It has also been found that coating of the drug particles with a surfactant, in particular a surfactant such as dipalmitoyl phosphatidylcholine (DPPC) or distearoyl phosphatidylcholine (DSPC) reproducibly improves delivery of the drug from the dry powder inhaler device. While coating aspirin with about 1.25% (w/w) surfactant resulted in little change in delivery from the inhaler (87%), surprisingly coating with 5% (w/w) surfactant result in an unexpected improvement such that 98% of the aspirin particles so coated were delivered from the dry powder inhaler. Thus, about 98%, about 99%, about 99.1%, about 99.2%, about 99.3%, about 99.4%, about 99.5%, about 99.6%, about 99.7%, about 99.8%, or about 99.9% of surfactant coated aspirin particles loaded into a dry powder inhaler can be reproducibly delivered from the inhaler device to the patient.

Pharmacokinetics of Aspirin

Aspirin is the acetylated form of salicylic acid, and the active chemical in aspirin is called acetylsalicylic acid (ASA). Aspirin is used by millions of people to achieve desirable effects, and by many people, baby aspirin is often used daily. The principal effect of aspirin is to impair the function of cyclooxygenase enzymes (specifically, COX1 and COX2 enzymes).

By inhibiting COX1, aspirin can irreversibly inhibit platelet aggregation, which decreases the risk of blood clots. Additionally, the impairment of the COX2 enzyme can reduce inflammation, stiffness, and pain in the body by inhibiting prostaglandins and thromboxanes. As such, individuals at high risk for heart attack, stroke, or with inflammation often take aspirin to address symptoms and effects of these conditions. As noted, aspirin can effectively reduce the likelihood of such myocardial events and reduce pain and inflammation with a dose as small as a baby aspirin. However, due at least in part to its inhibition of COX1, aspirin can increase the risk of bleeding and cause damage to organs such as the stomach and intestines, which can be painful.

Oral dosing with aspirin typically follows standard Michaelis-Menton kinetics. Following administration of an oral dose, peak plasma levels of salicylic acid, the primary metabolite of aspirin, are typically achieved after about 1-2 hours, and aspirin is generally undetectable within 1-2 hours after administration. The rate of absorption from the GI tract is dependent on a number of factors including the dosage form, presence or absence of food, gastric pH, as well as other factors.

Dry Powder Inhaler Technology

As stated above, the oral delivery of aspirin may create a risk of damage to the stomach wall leading to pain, indigestion and a high risk of bleeding. Further, according to at least one of the aspects of embodiments disclosed herein is the realization that it is often difficult to orally administer a drug during emergency situations that may implicate or result in a thromboembolic event. For example, the patient may be experiencing vomiting or otherwise be unable to take the drug orally. Additionally, oral administration of a drug may be undesirable because the drug does not reach the systemic blood stream immediately, thus delaying the important effects of the drug. Even so, due to the first pass effect in the liver and gut, the amount of drug reaching systemic circulation is much less than that administered. Therefore, according to aspects of various embodiments disclosed herein is the realization that an alternative route of administration could avoid these unwanted side effects.

Various embodiments disclosed herein reflect the novel realization that delivery of a drug by inhalation in the early stages of an emergency situation can provide a fast-acting, effective form of preliminary treatment of certain medical conditions. For example, in some embodiments, upon receiving a complaint of a symptom of a serious thromboembolic event, a patient can be administered, by DPI, a therapeutic amount of a NSAID. The NSAID can address problems associated with or provide an initial treatment for the medical condition.

However, dry powder inhalation of drugs has generally been limited by cough, to dosages of less than a milligram. Recent developments in particle engineering, in particular the development of PulmoSphere® technology, have enabled the delivery of a larger amount of dry powder to the lungs in a single actuation. See David E. Geller, M. D., et al., DEVELOPMENT OF AN INHALED DRY-POWDER FORMULATION OF TOBRAMYCIN USING PULMOSPHERE™ TECHNOLOGY, J Aerosol Med Pulm Drug Deliv. 2011 August; 24(4), pp. 175-82. In this publication, a dose of 112 mg tobramycin (in four capsules) was effectively delivered via PulmoSpheres®.

In accordance with some embodiments is the realization that the body includes various particle filters that limit the efficacy of inhaled drugs. For example, the oropharynx tends to prevent passage of particles having a diameter greater than 5 µm. However, in order to reach the alveoli, particles must have a size from about 1 µm to about 5 µm. Accordingly, some embodiments herein disclose the preparation and use of inhalable aspirin using technology similar to PulmoSpheres® to produce particles with a median geometric diameter of from about 1 µm to about 5 µm, and in some embodiments, from about 1.7 µm to about 2.7 µm. Generally, particles sizes between about 1 µm and about 3 µm effectively reach deposit in the alveolar spaces following inhalation. The portion of the drug formulation falling within this size range is typically referred to as the fine particle fraction (FPF) and higher FPFs are most desirable when producing an inhalable drug formulation. In some cases, the FPF in the present invention can range from about 20% to about 90%, or even higher, depending on a number of factors including the method used to micronize the aspirin as well as optional excipients that may be included in the formulation that modulate aerodynamic performance.

Similar results are observed for other drugs, such as pharmaceutically active proteins, for example insulin. In the case of insulin, delivery by inhalation not only provides significantly higher peak plasma levels as compared to delivery by injection (nearly double), but a substantially more rapid appearance of the molecule in the circulation (less than 30 minutes when inhaled versus about 90 minutes when injected) (Technosphere® Technology: A Platform for Inhaled Protein Therapeutics, in Pulmonary Delivery: Innovative Technologies Breathing New Life into Inhalable Therapeutics, available online at http://www.ondrugdelivery.com, pp. 8-11).

There has been no single dose use of aspirin by dry powder inhaler to replace the traditional daily use of a NSAID (such as a baby aspirin) or emergency use of a NSAID as preventative care for symptoms of a thromboembolic event. Accordingly, some embodiments disclosed herein provide methods for administering a NSAID by dry powder inhalation in an amount less than the dosage of a baby aspirin (e.g., less than 81 mg).

Therefore, in some embodiments, a method for treating disease, e.g., by reducing the risk of a thromboembolic event, can be provided, which comprises administering a NSAID, such as a salicylate, by a DPI or MDI. For example, the method can comprise administering acetylsalicylic acid by a DPI or MDI. The administered dosage can be less than 25 mg of acetylsalicylic acid. Further, the administered dosage can be less than 20 mg of acetylsalicylic acid. The administered dosage can be less than 15 mg of acetylsalicylic acid. The administered dosage can also be less than 12 mg of acetylsalicylic acid. The administered dosage can be less than 10 mg of acetylsalicylic acid. Furthermore, the administered dosage can be less than 8 mg of acetylsalicylic acid. The administered dosage can be less than 5 mg of acetylsalicylic acid. In some embodiments, the administered dosage can be less than 2 mg of acetylsalicylic acid.

For example, according to some embodiments, the dosage can be from about 2 mg to about 30 mg of acetylsalicylic acid. In some embodiments, the dosage can be from about 4 mg to about 25 mg of acetylsalicylic acid. The dosage can be from about 6 mg to about 20 mg of acetylsalicylic acid. Further, in some embodiments, the dosage can be from about 8 mg to about 15 mg of acetylsalicylic acid. Further, in some embodiments, the dosage can be from about 10 mg to about 13 mg of acetylsalicylic acid. For example, in some embodiments, the dosage can be about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of acetylsalicylic acid.

Additionally, the dose of acetylsalicylic acid can be less than about 80 mg. In some embodiments, the dose of acetylsalicylic acid can be from about 1 mg to about 75 mg. In some embodiments, the dose of acetylsalicylic acid can be from about 2 mg to about 60 mg. In some embodiments, the dose of acetylsalicylic acid can be from about 5 mg to about 40 mg. In some embodiments, the dose of acetylsalicylic acid can be from about 10 mg to about 30 mg. In some embodiments, the dose of acetylsalicylic acid can be from about 12 mg to about 25 mg. In some embodiments, the dose of acetylsalicylic acid can be from about 15 mg to about 20 mg.

In accordance with some embodiments, such dosages can provide a bioequivalent dosage when compared to typical dosages of about 81 mg to about 325 mg, while demonstrating few negative side effects.

Thus, in some embodiments, a NSAID, such as aspirin, can be administered by DPI or MDI in a single dose that is much less than a traditional oral dose of aspirin, which can provide a bioequivalent equivalent treatment while tending to avoid the negative side effects associated with some NSAIDs, such as aspirin. Further, systems of administering such treatments are also provided.

In some embodiments, a NSAID, such as aspirin, can be administered by DPI or MDI in multiple inhalation doses. For example, aspirin may be inhaled in 1-6, 2-6, 3-6, 4-6, 2-3, 2, 3, 4, 5, or 6 inhalations. The number of inhalations may be dependent on the amount of ASA present in each chamber of the DPI and/or the total amount of ASA to be delivered. For example, 25 mg, 30 mg, 35 mg, 40 mg, 50 mg, 25-40 mg, 25-50 mg of ASA may be delivered to the subject in 2 to 3 inhalations by DPI.

In some embodiments, the NSAID, in particular aspirin, can be formulated to include pharmaceutically acceptable excipients that are effective to improve aerodynamic performance, bioavailability and/or pharmacokinetics as compared to prior art methods of administration.

The DPI or MDI can have a mouthpiece and an actuation member for making available the NSAID for inhalation by a patient to reduce the risk of the thromboembolic event.

For example, according to some embodiments, a method of reducing the risk of a thromboembolic event is provided and can comprise administering a dose of a non-steroidal anti-inflammatory drug by a dry powder inhaler. The dose can be effective to reduce a risk of a thromboembolic event in a patient. The dry powder inhaler can have a mouthpiece and an actuation member for making available the dose of the non-steroidal anti-inflammatory drug for inhalation by the patient to reduce the risk of the thromboembolic event.

A drug delivery system can also be provided according to some embodiments, for treating a disease, for example, by reducing the risk of a thromboembolic event. The system can comprise a dose of a non-steroidal anti-inflammatory drug in powder form. The dose can be effective to reduce a risk of a thromboembolic event in a patient. The system can also comprise a dry powder inhaler. The dry powder inhaler can have a mouthpiece, a reservoir for receiving the dose of the non-steroidal anti-inflammatory drug, and an actuation member for making available the dose of the non-steroidal anti-inflammatory drug for inhalation by the patient through the mouthpiece.

In some embodiments, the thromboembolic event comprises at least one of myocardial infarction, deep venous thrombosis, pulmonary embolism, or thrombotic stroke. The dose of the non-steroidal anti-inflammatory drug can be administered as a preliminary treatment in response to a symptom of a thromboembolic event. The non-steroidal anti-inflammatory drug can comprise aspirin. Further, the dose of the non-steroidal anti-inflammatory drug can be administered in a single dose.

2. DEFINITIONS

The term "about", as used here, refers to +/−5% of a value.

The term "dry powder" as used herein refers to a composition contains finely dispersed respirable dry particles that are capable of being dispersed in an inhalation device and subsequently inhaled by a subject. Such dry powder or dry particle may contain up to about 15% water or other solvent, or be substantially free of water or other solvent, or be anhydrous.

The term "dry particles" as used herein refers to respirable particles that may contain up to about 15% water or other solvent, or be substantially free of water or other solvent, or be anhydrous.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 μm, preferably about 5 μm or less.

As used herein, the terms "administration" or "administering" of respirable dry particles refers to introducing respirable dry particles to the respiratory tract of a subject.

The term "dispersible" is a term of art that describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by HELOS/RODOS. These quotients are referred to herein as "1/4 bar," and "0.5/4 bar," respectively, and dispersibility correlates with a low quotient. For example, 1/4 bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a 1/4 bar or 0.5/4 bar ratio that is close to 1.0. Highly dispersible powders have a low tendency to agglomerate, aggregate or clump together and/or, if agglomerated, aggregated or clumped together, are easily dispersed or deagglomerated as they emit from an inhaler and are breathed in by the subject. Dispersibility can also be assessed by measuring the size emitted from an inhaler as a function of flow rate.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia Convention, Rockville, Md., 13$^{th}$ Revision, 222-225, 2007. This method utilizes an in vitro device set up to mimic patient dosing.

The terms "FPF (<5.6)," "FPF (<5.6 µm)," and "fine particle fraction of less than 5.6 µm" as used herein, refer to the fraction of a sample of dry particles that have an aerodynamic diameter of less than 5.6 µm. For example, FPF (<5.6) can be determined by dividing the mass of respirable dry particles deposited on the stage one and on the collection filter of a two-stage collapsed Andersen Cascade Impactor (ACI) by the mass of respirable dry particles weighed into a capsule for delivery to the instrument. This parameter may also be identified as "FPF_TD (<5.6)," where TD means total dose. A similar measurement can be conducted using an eight-stage ACI. The eight-stage ACI cutoffs are different at the standard 60 L/min flow rate, but the FPF_TD (<5.6) can be extrapolated from the eight-stage complete data set. The eight-stage ACI result can also be calculated by the USP method of using the dose collected in the ACI instead of what was in the capsule to determine FPF.

The terms "FPF (<3.4)," "FPF (<3.4 µm)," and "fine particle fraction of less than 3.4 µm" as used herein, refer to the fraction of a mass of respirable dry particles that have an aerodynamic diameter of less than 3.4 µm. For example, FPF (<3.4) can be determined by dividing the mass of respirable dry particles deposited on the collection filter of a two-stage collapsed ACI by the total mass of respirable dry particles weighed into a capsule for delivery to the instrument. This parameter may also be identified as "FPF_TD (<3.4)," where TD means total dose. A similar measurement can be conducted using an eight-stage ACI. The eight-stage ACI result can also be calculated by the USP method of using the dose collected in the ACI instead of what was in the capsule to determine FPF.

The terms "FPF (<5.0)," "FPF (<5.0 µm)," and "fine particle fraction of less than 5.0 µm" as used herein, refer to the fraction of a mass of respirable dry particles that have an aerodynamic diameter of less than 5.0 µm. For example, FPF (<5.0) can be determined by using an eight-stage ACI at the standard 60 L/min flow rate by extrapolating from the eight-stage complete data set. This parameter may also be identified as "FPF_TD (<5.0)," where TD means total dose.

The term "nanoparticles" refers to particles that have a single crystallite grain between about 1 nm to about 900 nm, preferably between about 5 nm to about 500 nm. Individual grains can agglomerate into clusters/agglomerates.

The term "excipient" refers to a pharmacologically inactive substance formulated with the active ingredient ("API") of a medication.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

3. NON-STEROIDAL ANTI-INFLAMMATORY DRUGS (NSAIDs)

NSAIDs, such as aspirin, can provide various beneficial effects and contribute to reducing the risk of a cardiovascular disease (such as thrombosis). However, the use of NSAIDs, such as aspirin, in a clinical setting has traditionally been limited to oral administration. Oral administration of aspirin, for example, can result in the loss or inactivation of approximately ⅔ of the oral dosage due to the first pass effect in the gut and liver. While one third of the dosage reaches the systemic blood stream and provides the desired effect, the negative side effects created by the full dosage often deter patients from using aspirin on a regular or daily basis.

Further, in many situations, such as in emergencies, oral administration of NSAIDs, such as aspirin, may be inappropriate because it may take too long to be effective. According to at least one aspect of some embodiments disclosed herein is the realization that an alternative administration method and systems can be implemented that utilize a lower dosage and provide a more direct delivery mechanism to the systemic blood stream. Thus, some embodiments disclosed herein allow for the beneficial effects of NSAIDs, such as aspirin, to be achieved on a regular basis and in emergency situations, while minimizing previous drawbacks associated with the use of NSAIDs.

Various studies have determined that aspirin has a significant effect on reducing the risk of myocardial infarction. However, these studies presented inconclusive data on strokes, pulmonary embolism, or deep venous thrombosis. These studies have used aspirin dosages of 325 mg. However, these studies have based their findings on oral administration of aspirin and have not suggested DPI or MDI pathways, which are provided in some embodiments disclosed herein. Further, the administration of aspirin has negative side effects, such as significantly increasing major gastrointestinal and extracranial bleeds by over 50%. This has led some to argue that for preventative treatment, aspirin is of uncertain net value.

Further studies have tested whether the benefits of aspirin could be obtained at low dosages, such as that of baby aspirin (i.e., 81 mg). The Swedish Aspirin Low-dose Trial (SALT) found that a low dose (75 mg/day) of aspirin significantly reduces the risk of stroke or death in patients with cerebrovascular ischemic events. However, the study also reported gastrointestinal side effects that included a significant excess of bleeding episodes. A Danish study found that patients receiving aspirin as an antithrombotic agent achieved satisfactory platelet inhibition with 50 mg/day, while the remainder of the patients needed over 50 mg/day. Furthermore, a Dutch TIA Study concluded that aspirin at any dose above 30 mg daily prevents 13% of vascular events, and that there is a need for more efficacious drugs. However, no study or teaching has been provided regarding the administration of aspirin by DPI or MDI at very low doses.

The effectiveness of low dose ASA administration depends on many factors, including the route of administration, patient demographics including weight, age, etc., and the bioavailability of ASA during a specific time period. Many patients who are prescribed low-dose enteric-coated aspirin for secondary prevention of cardiovascular events have persistent uninhibited platelet COX activity. Younger and heavier patients and those with a previous MI are most likely to have an inadequate response to treatment. (J. Am. Coll. Cardiol. 2005; 47:1258-1263). As shown by Bode-Böger et al., plain and enteric-coated formulations of 100 mg ASA are equally effective in inhibiting platelet aggregation, platelet thromboxane production, and urinary 2,3-dinor-TXB2 excretion rates. In contrast, a very low dose of 40 mg of ASA was significantly less effective in inhibiting these indices of platelet activation in healthy human subjects. It was suggested that 40 mg of ASA (p) may be too low to inhibit sufficiently platelet activity in cardiovascular diseases in whom platelet activity is increased. (European Journal of Clinical Pharmacology, 1998, Vol. 54, Issue 9-10, pp 707-714.) Surprisingly, the present invention provides an approach to deliver an effective method of treatment using low dose ASA.

Although inhaled dry powder formulations of aspirin have been developed, reports have stated that the formulation was not clinically feasible because it is difficult to meet the high dosage requirements of aspirin (~80 mg/day for low-dose prevention of coronary events and stroke, and at least 300 mg/day for pain or fever relief) via pulmonary delivery of dry powders.

In addition, these reports recognize that adverse effects of dry powder on the lungs, such as coughing, cannot be avoided unless the doses are less than a few tenths of a milligram in a single breath. Thus, prior teachings suggest that higher dosage requirements of aspirin would be impossible to meet using DPI. Finally, some have taught that there is a higher incidence of aspirin intolerance in asthmatic patients when aspirin is delivered by inhalation than orally.

In yet another study, the authors noted that use of nanoparticulate drugs for dry powder inhaler (DPI) delivery is not straightforward. Direct inhalation of nanoparticulate drugs was infeasible due to their small size. The nanometer size leads to the nanoparticulate drugs being predominantly exhaled from the lungs, without any deposition in the lungs taking place. Moreover, a severe aggregation problem arising from the small size makes their physical handling difficult for DPI delivery. Accordingly, "large hollow carrier particles" of nanoparticulate drugs has been developed for pulmonary delivery of some drugs. See Hadinoto et al., *Drug Release Study Of Large Hollow Nanoparticulate Aggregates Carrier Particles For Pulmonary Delivery*, International Journal of Pharmaceutics 341 (2007) 195-20.

In the Hadinoto study, the authors used aspirin as a model for "lowly water-soluble" drugs. The authors acknowledged that "with regard to the aspirin, the nanoparticulate polymer delivery method is not the most suitable method of delivery due to the high dosage requirement of aspirin (~300 mg/day)," and overall, the aim of the study was to identify key facets in the formulation of the large hollow nanoparticulate aggregates. See id.

In some embodiments of the inventions disclosed herein, methods and systems are provided for treating (including prophylactic treatment or reducing the risk of) a disease, for example, treating a cardiovascular disease (such as thrombosis) by administration of a very low amount of a NSAID, such as a low dose of aspirin, by DPI. The dose can be much less than that of a baby aspirin (e.g., less than 81 mg). The administered dosage can be less than about 40 mg of acetylsalicylic acid. The administered dosage can be less than 25 mg of acetylsalicylic acid. Further, the administered dosage can be less than 20 mg of acetylsalicylic acid. The administered dosage can be less than 15 mg of acetylsalicylic acid. The administered dosage can also be less than 12 mg of acetylsalicylic acid. The administered dosage can be less than 10 mg of acetylsalicylic acid. Furthermore, the administered dosage can be less than 8 mg of acetylsalicylic acid. The administered dosage can be less than 5 mg of acetylsalicylic acid. In some embodiments, the administered dosage can be less than 2 mg of acetylsalicylic acid.

For example, according to some embodiments, the dosage can be from about 1 mg to about 40 mg. In some embodiments, the dosage can be from about 4 mg to about 25 mg of acetylsalicylic acid. The dosage can be from about 6 mg to about 20 mg of acetylsalicylic acid. Further, in some embodiments, the dosage can be from about 8 mg to about 15 mg of acetylsalicylic acid. Further, in some embodiments, the dosage can be from about 10 mg to about 13 mg of acetylsalicylic acid. For example, in some embodiments, the dosage can be about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of acetylsalicylic acid.

Additionally, the dose of acetylsalicylic acid can be less than about 80 mg. In some embodiments, the dose of acetylsalicylic acid can be from about 1 mg to about 75 mg. In some embodiments, the dose of acetylsalicylic acid can be from about 2 mg to about 60 mg. In some embodiments, the dose of acetylsalicylic acid can be from about 5 mg to about 40 mg. In some embodiments, the dose of acetylsalicylic acid can be from about 10 mg to about 30 mg. In some embodiments, the dose of acetylsalicylic acid can be from about 12 mg to about 25 mg. In some embodiments, the dose of acetylsalicylic acid can be from about 15 mg to about 20 mg.

Such dosages can provide a bioequivalent dosage when compared to typical dosages of 81 mg to about 325 mg, while demonstrating few negative side effects.

In some embodiments, NSAIDs can be used in various methods and systems. In some embodiments, NSAIDs can include salicylates, i.e., the salts and esters of salicylic acid, which have anti-platelet action. Further, NSAIDs can also include one or more of the following in Table 1:

TABLE 1

Examples of NSAIDS

Aspirin (Aspirin is a brand name; the chemical is called acetylsalicylic acid)
Celecoxib (Celebrex)
Dexdetoprofen (Keral)
Diclofenac (Voltaren, Cataflam, Voltaren-XR)

TABLE 1-continued

Examples of NSAIDS

Diflunisal (Dolobid)
Etodolac (Lodine, Lodine XL)
Etoricoxib (Algix)
Fenoprofen (Fenopron, Nalfron)
Firocoxib (Equioxx, Previcox)
Flurbiprofen (Urbifen, Ansaid, Flurwood, Froben)
Ibuprofen (Advil, Brufen, Motrin, Nurofen, Medipren, Nuprin)
Indomethacin (Indocin, Indocin SR, Indocin IV)
Ketoprofen (Actron, Orudis, Oruvail, Ketoflam)
Ketorolac (Toradol, Sprix, Toradol IV/IM, Toradol IM)
Licofelone (under development)
Lornoxicam (Xefo)
Loxoprofen (Loxonin, Loxomac, Oxeno)
Lumiracoxib (Prexige)
Meclofenamic acid (Meclomen)
Mefenamic acid (Ponstel)
Meloxicam (Movalis, Melox, Recoxa, Mobic)
Nabumetone (Relafen)
Naproxen (Aleve, Anaprox, Midol Extended Relief, Naprosyn, Naprelan)
Nimesulide (Sulide, Nimalox, Mesulid)
Oxaporozin (Daypro, Dayrun, Duraprox)
Parecoxib (Dynastat)
Piroxicam (Feldene)
Rofecoxib (Vioxx, Ceoxx, Ceeoxx)
Salsalate (Mono-Gesic, Salflex, Disalcid, Salsitab)
Sulindac (Clinoril)
Tenoxicam (Mobiflex)
Tolfenamic acid (Clotam Rapid, Tufnil)
Valdecoxib (Bextra)

Other active ingredients can also be used instead of, or in combination with, a NSAID in the methods and systems disclosed herein. Such active ingredients include Plavix (clopidogrel), COX-2 inhibitors, other remedies such as Nattokinase (an enzyme (EC 3.4.21.62, extracted and purified from a Japanese food called nattō)), antithrombotics, antiplatelet antibodies, and anticoagulants (e.g., Coumadin (warfarin)). Further, other drugs that provide different beneficial effects, such as being effective to reduce a risk of a cardiovascular disease (such as thrombosis) in a patient, can also be used in some embodiments. For example, a NSAID (e.g., aspirin) may be combined with one or more of a platelet aggregation inhibitor (e.g., aspirin+omeprazole, cangrelor, vorapaxer); anticoagulant (e.g., altepase, ardeparin, dalteparin, danaparoid, enoxaparin, fondaparinux, lepirudin, urokinase, warfarin, adomiparin, tecafarin, AZD0837, edoxaban, preluent, betrixaban); and/or fibronolytics (e.g., desmoleplase, THR-100, recomodulin, EP217609, ISIS-Fx Rx).

In some instances, two or more active ingredients that are not NSAIDs are combined in the methods and systems disclosed herein. For example, any combination of two or more active ingredients including Plavix (clopidogrel), COX-2 inhibitors, other remedies such as Nattokinase (an enzyme (EC 3.4.21.62, extracted and purified from a Japanese food called nattō)), antithrombotics, antiplatelet antibodies, and anticoagulants (e.g., Coumadin (warfarin)), may be combined in the methods and systems disclosed herein.

The dose of the active ingredient that is not an NSAID will be determined by one skilled in the art, based upon relevant factors such as the general health and well-being, the weight, age, and medical history of the patient. The dose of each active ingredient may be determined individually, or may be adjusted based on the dose of any other active ingredient that it may be combined with. As provided below, the dose administered per day may refer to the amount delivered per inhalation in an emergency administration, or the amount delivered daily for prophylactic treatment. Thus, administration per day may refer to the dose administered during emergency treatment in a single day, without repeat administration after the emergency event has resolved.

The dose of the active ingredient that is not an NSAID may be at least about 5 mg/day, at least about 10 mg/day, at least about 20 mg/day, at least about 30 mg/day, at least about 40 mg/day, at least about 50 mg/day, at least about 60 mg/day, at least about 70 mg/day, at least about 80 mg/day, at least about 90 mg/day, at least about 100 mg/day, at least about 110 mg/day, at least about 120 mg/day, at least about 130 mg/day, at least about 140 mg/day, at least about 150 mg/day, at least about 175 mg/day, at least about 200 mg/day, at least about 250 mg/day, at least about 300 mg/day.

The total dose of the one or more active ingredients (e.g., NSAID in combination with an active ingredient that is not an NSAID) may be about 10-300 mg/day, about 10-200 mg/day, about 10-150 mg/day, about 10-100 mg/day, about 10-75 mg/day, about 10-50 mg/day, about 10-40 mg/day.

The total dose of the one or more active ingredients may from about 1 mg to about 40 mg. In some embodiments, the dosage can be from about 4 mg to about 25 mg of active ingredient. The dosage can be from about 6 mg to about 20 mg of active ingredient. Further, in some embodiments, the dosage can be from about 8 mg to about 15 mg of active ingredient. Further, in some embodiments, the dosage can be from about 10 mg to about 13 mg of active ingredient. For example, in some embodiments, the dosage can be about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of active ingredient.

In some embodiments comprising clopidogrel as an active ingredient, the dose of clopidogrel may be at least about 40 mg per day, 50 mg per day, at least about 60 mg per day, at least about 70 mg per day, at least about 75 mg per day, at least about 80 mg per day, at least about 90 mg per day, at least about 100 mg per day, at least about 110 mg per day, at least about 120 mg per day, at least about 130 mg per day, at least about 140 mg per day, at least about 150 mg per day, or at least about 300 mg per day.

When clopidogrel is dosed with aspirin, the dose may be about 75 mg clopidogrel and about 75-325 mg aspirin, about 75 mg clopidogrel and about 75-162 mg aspirin, or about 75 mg clopidogrel and about 81-162 mg aspirin.

Thus, the discussion of methods and systems shall apply generally to these various alternatives, although for discussion purposes, the present disclosure often refers to aspirin. It is contemplated that the methods, effects, pharmacokinetic data, and other considerations relating to aspirin can be equally applied to other NSAIDs, according to some embodiments.

4. DRY POWDERS AND DRY PARTICLES

The subject technology relates to respirable dry powders and dry particles that comprise an NSAID, such as acetylsalicylic acid, as an active ingredient, and optionally one or more additional active ingredients. For example, the NSAID may be combined with one or more of a platelet aggregation inhibitor, an anticoagulant, fibronolytic, and/or antithrombotic.

In one aspect, the respirable dry powder comprises aspirin and at least one of a platelet aggregation inhibitor, an anticoagulant, an antithrombotic and/or a fibronolytic.

In one aspect, the respirable dry powder comprises aspirin and an antithrombotic. The antithrombotic may be any antithrombotic known by one skilled in the art, for example, Plavix (clopidogrel), Lovenox (enoxaparin sodium), Pradaxa (dabigatran etexilate mesylate), Pletal (cilostazol), Aggrenox (aspirin/extended-release dipyridamole), Activase (alteplase), Angiomax (bivalirudin), Arixtra (fondaparinux sodium), Effient (prasugrel), Brilinta (ticagrelor), Xarelto (Rivaroxaban), Eliquis (apixaban), and combinations thereof.

In another aspect, the respirable dry powder comprises aspirin and an anticoagulant. The anticoagulant may be, for example, heparin, a vitamin K antagonist, a direct thrombin inhibitor, a direct factor Xa inhibitor, and combinations thereof.

The respirable dry powder may comprise aspirin and Coumadin (warfarin).

The respirable dry powder may comprise aspirin and Plavix (clopidogrel).

The subject technology also relates to respirable dry powders and dry particles that comprise one or more active ingredients, wherein the active ingredient is not an NSAID. For example, the respirable dry powders and dry particles may comprise any combination of a platelet aggregation inhibitor, an anticoagulant, fibronolytic, and/or antithrombotic.

In one aspect, the dry particles of the subject technology are small, and preferably are dispersible. The size of the dry particles can be expressed in a variety of ways that are conventional in the art, such as, fine particle fraction (FPF), volumetric median geometric diameter (VMGD), or mass median aerodynamic diameter (MMAD).

In certain embodiments, the dry particles of the subject technology are small and preferably dispersible. For example, the dry particles of the subject technology may have a VMGD as measured by HELOS/RODOS at 1.0 bar of about 10 μm or less (e.g., about 0.1 μm to about 10 μm). Preferably, the dry particles of the subject technology have an VMGD of about 9 μm or less (e.g., about 0.1 μm to about 9 μm), about 8 μm or less (e.g., about 0.1 μm to about 8 μm), about 7 μm or less (e.g., about 0.1 μm to about 7 μm), about 6 μm or less (e.g., about 0.1 μm to about 6 μm), about 5 μm or less (e.g., less than 5 μm, about 0.1 μm to about 5 μm), about 4 μm or less (e.g., 0.1 μm to about 4 μm), about 3 μm or less (e.g., 0.1 μm to about 3 μm), about 2 μm or less (e.g., 0.1 μm to about 2 μm), about 1 μm or less (e.g., 0.1 μm to about 1 μm), about 0.5 μm to about 6 μm, about 0.5 μm to about 5 μm, about 0.5 μm to about 4 μm, about 0.5 μm to about 3 μm, or about 0.5 μm to about 2 μm as measured by HELOS/RODOS at 1.0 bar. In an exemplary embodiment, the dry particles of the subject technology have a VMGD as measured by HELOS/RODOS at 1.0 bar of about 1.3 to about 1.7 μm. In another exemplary embodiment, the dry particles of the subject technology have a VMGD as measured by HELOS/RODOS at 1.0 bar of about 0.5 μm to about 2 μm.

In certain embodiments, the dry particles of the subject technology are large and preferably dispersible. For example, the dry particles of the subject technology may have a VMGD as measured by HELOS/RODOS at 1.0 bar of about 30 μm or less (e.g., about 5 μm to about 30 μm). Preferably, the dry particles of the subject technology have an VMGD of about 25 μm or less (e.g., about 5 μm to about 25 μm), about 20 μm or less (e.g., about 5 μm to about 20 μm), about 15 μm or less (e.g., about 5 μm to about 15 μm), about 12 μm or less (e.g., about 5 μm to about 12 μm), about 10 μm or less (e.g., about 5 μm to about 10 μm), or about 8 μm or less (e.g., 6 μm to about 8 μm) as measured by HELOS/RODOS at 1.0 bar.

The dry powders described herein can comprise a mixture of large particles and small particles.

Preferably, whether the particles are small or large, the dry particles of the subject technology are dispersible, and have 1/4 bar and/or 0.5/4 bar of about 2.2 or less (e.g., about 1.0 to about 2.2) or about 2.0 or less (e.g., about 1.0 to about 2.0). Preferably, the dry particles of the subject technology have 1/4 bar and/or 0.5/4 bar of about 1.9 or less (e.g., about 1.0 to about 1.9), about 1.8 or less (e.g., about 1.0 to about 1.8), about 1.7 or less (e.g., about 1.0 to about 1.7), about 1.6 or less (e.g., about 1.0 to about 1.6), about 1.5 or less (e.g., about 1.0 to about 1.5), about 1.4 or less (e.g., about 1.0 to about 1.4), about 1.3 or less (e.g., less than 1.3, about 1.0 to about 1.3), about 1.2 or less (e.g., 1.0 to about 1.2), about 1.1 or less (e.g., 1.0 to about 1.1 μm) or the dry particles of the subject technology have 1/4 bar of about 1.0.

Alternatively or in addition, the respirable dry particles of the subject technology can have an MMAD of about 10 μm or less, such as an MMAD of about 0.5 μm to about 10 μm. Preferably, the dry particles of the subject technology have an MMAD of about 5 μm or less (e.g. about 0.5 μm to about 5 μm, preferably about 1 μm to about 5 μm), about 4 μm or less (e.g., about 1 μm to about 4 μm), about 3.8 μm or less (e.g. about 1 μm to about 3.8 μm), about 3.5 μm or less (e.g. about 1 μm to about 3.5 μm), about 3.2 μm or less (e.g. about 1 μm to about 3.2 μm), about 3 μm or less (e.g. about 1 μm to about 3.0 μm), about 2.8 μm or less (e.g. about 1 μm to about 2.8 μm), about 2.2 μm or less (e.g. about 1 μm to about 2.2 μm), about 2.0 μm or less (e.g. about 1 μm to about 2.0 μm) or about 1.8 μm or less (e.g. about 1 micron to about 1.8 μm).

Alternatively or in addition, the dry powders and dry particles of the subject technology have a FPF of less than 5.0 μm (FPF_TD<5.0 μm) of at least about 20%, at least about 30%, at least about 45%, preferably at least about 40%, at least about 45%, at least about 50%, at least about 60%, at least about 65% or at least about 70%. Alternatively or in addition, the dry powders and dry particles of the subject technology have a FPF of less than 5.0 μm of the emitted dose (FPF_ED<5.0 μm) of at least about 45%, preferably at least about 50%, at least about 60%, at least about 65%, at least about 70%, at least about 75%, at least about 80%, or at least about 85%.

Alternatively or in addition, the respirable dry powders and dry particles of the invention can have an FPF of less than about 5.6 μm (FPF<5.6 μm) of at least about 20%, at least about 30%, at least about 40%, preferably at least about 45%, at least about 50%, at least about 55%, at least about 60%, at least about 65%, or at least about 70%.

Alternatively or in addition, the dry powders and dry particles of the invention can have an FPF of less than about 3.4 μm (FPF<3.4 μm) of at least about 20%, preferably at least about 25%, at least about 30%, at least about 35%, at least about 40%, at least about 45%, at least about 50%, or at least about 55%.

Alternatively or in addition, the respirable dry powders and dry particles of the subject technology have a tap density of about 0.1 $g/cm^3$ to about 1.0 $g/cm^3$. For example, the small and dispersible dry particles have a tap density of about 0.1 $g/cm^3$ to about 0.9 $g/cm^3$, about 0.2 $g/cm^3$ to about 0.9 $g/cm^3$, about 0.2 $g/cm^3$ to about 0.9 $g/cm^3$, about 0.3 $g/cm^3$ to about 0.9 $g/cm^3$, about 0.4 $g/cm^3$ to about 0.9 $g/cm^3$, about 0.5 $g/cm^3$ to about 0.9 $g/cm^3$, or about 0.5 $g/cm^3$ to about 0.8 $g/cm^3$, greater than about 0.4 g/cc, greater than about 0.5 g/cc, greater than about 0.6 g/cc, greater than about 0.7 g/cc, about 0.1 g/cm$^3$ to about 0.8 g/cm$^3$, about 0.1 g/cm$^3$ to about 0.7 g/cm$^3$, about 0.1 g/cm$^3$ to about 0.6 g/cm$^3$, about 0.1 g/cm$^3$ to about 0.5 g/cm$^3$, about 0.1 g/cm$^3$ to about 0.4 g/cm$^3$, about 0.1 g/cm$^3$ to about 0.3 g/cm$^3$, less than 0.3 g/cm$^3$. In a preferred embodiment, tap density is greater than about 0.4 g/cm$^3$. In another preferred embodiment, tap density is greater than about 0.5 g/cm$^3$. Alternatively, tap density is less than about 0.4 g/cm$^3$.

Alternatively or in addition, the respirable dry powders and dry particles of the subject technology can have a water or solvent content of less than about 15% by weight of the respirable dry particle. For example, the respirable dry particles of the subject technology can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The respirable dry particles of the subject technology can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5% about 5%.

Depending on the specific applications of the dry powders described herein, the dry powder and particles may contain a low or high percentage of active ingredient in the composition. For example, the dry particles may contain 3% or more, 5% or more, 10% or more, 15% or more, 20% or more, 25% or more, 30% or more, 35% or more, 40% or more, 50% or more, 60% or more, 70% or more, 75% or more, 80% or more, 85% or more, 90% or more, or 95% or more (weight percentage) of the active ingredient (e.g., acetylsalicylic acid).

5. DELIVERY OF DRY POWDERS

Through some of the embodiments disclosed herein, Applicants have overcome the challenges acknowledged by prior teachings. In particular, Applicants have recognized that when a drug is inhaled into the lungs, the drug can be dispersed toward the alveoli. Although alveoli primarily function to exchange carbon dioxide for oxygen, alveoli also produce enzymes. Thus, inhaled substances, such as pathogens, drugs, or other chemicals, may be processed at the alveoli.

An alveolus comprises a network of elastic fibers and capillaries, resembling a woven sphere on its outer surface. The capillaries function to carry oxygen depleted blood toward the lungs and oxygen rich blood away from the lungs, via the pulmonary artery and the pulmonary vein. The interior of each alveolus comprises a thin tissue known as an alveolar lining or epithelium. Alveolar epithelium is made of two distinct types of cells, known as flat type I and type II. Flat type I cells cover most of the surface area of the epithelium and are closely spaced, allowing only small molecules to pass therebetween, such as oxygen and carbon dioxide. Type II alveolar cells aid in producing the pulmonary surfactant used in gas exchange. Further, the alveolar epithelium also comprises macrophages, which assist in disposing of fine particulate foreign matter such as dust, tar, and pathogens. Despite the diminutive size of the alveoli (being only approximately 250 µm), because an adult can have between 200 million and 400 million alveoli, the alveolar respiratory surface area can be from approximately 1,400 to about 1,600 square feet.

According to some embodiments disclosed herein, absorption of NSAIDs administered by DPI or MDI through the pulmonary capillaries and epithelium can provide an immediately effective treatment to address symptoms of thromboembolic events. One of the novel realizations of some embodiments is that the substantial first pass effect produced by oral administration of NSAIDs, such as aspirin, can be avoided through administration by dry powder inhaler. In addition, there has hitherto been no teaching or suggestion regarding the pharmacokinetics of dry powder delivery of a NSAID, such as aspirin, and the possible metabolism or inactivation of the drug as it encounters the endothelial tissue of the pulmonary capillaries.

The delivery of a NSAID by DPI or MDI is a complex and unpredictable technological area that has not provided straightforward or expected results to a person of skill in the art. Accordingly, there has been no reason for a person of skill to believe that a combination of prior systems or treatment methods could produce the embodiments disclosed herein. For example, some embodiments herein recognize an unexpected result that as a drug crosses the endothelium of pulmonary arteries and alveoli, the first pass effect is minimized and results in a much lower rate of the activation of the drug than in other drug delivery pathways.

The endothelium of the pulmonary capillaries serves as a barrier by selectively allowing materials to exit or enter the bloodstream. It would be expected that aspirin would be inactivated in the pulmonary capillaries, which are lined by endothelial cells. The endothelial cells are extremely metabolically active. Thus, a person of skill would expect that aspirin would be inactivated by the endothelium of the pulmonary capillaries. However, according to some embodiments disclosed herein, it is contemplated that as the powdered drug encounters the endothelium, the endothelium can metabolize or activate a much smaller portion of the powdered drug compared to the metabolism provided by the gut and liver. For example, after being transformed in the stomach to salicylic acid, as much as 80% of the salicylic acid is metabolized in the liver. Thus, only a small minority of the salicylic acid is bioavailable to the systemic blood stream.

However, it is contemplated that a vast majority of the salicylic acid metabolized from the inhaled aspirin powder will be bioavailable to the systemic blood stream. Thus, a dose of much less than that of a baby aspirin (e.g., less than 81 mg) can be provided by dry powder inhalation. This can provide a much lower dosage while providing a bioequivalent dosage.

Further, in accordance an aspect of some embodiments, it is contemplated that an analogous first pass effect may be experienced in the endothelium of the pulmonary capillaries. Accordingly, with regard to the provision of an inhaled dosage that is the bioequivalent of a baby aspirin administered orally, the inhaled dosage should account for some first pass effect experience through the endothelium of the pulmonary capillaries.

In accordance with some embodiments, the first pass effect through the endothelium of the pulmonary capillaries can be a minimum, which provides little overall effect on the inhaled dosage.

However, it is also contemplated that in some embodiments, the first pass effect through the endothelium of the pulmonary capillaries can be entirely negligible. Thus, the amount of the inhaled dosage need not be adjusted to compensate for first pass effect through the pulmonary capillaries.

Therefore, some embodiments recognize the unexpected result that even extremely low doses of aspirin (and likely other NSAIDs) can provide a significant therapeutic effect while providing de minimus or inconsequential side effects. For example, doses as low as 1 mg, 2 mg, 3 mg, 4 mg, or 5 mg of acetylsalicylic acid can be effective in reducing the risk of a thromboembolic event. Accordingly, the net benefits increased dramatically at significantly lower doses, according to some embodiments. These results and outcomes are unexpected given the complex and unpredictable nature of drug interactions in the body, drug delivery pathways, and microscopic drug structures. Finally, no teachings or other prior references disclose a system or process for achieving therapeutically beneficial results while substantially avoiding any negative side effects using DPI or MDI drug delivery mechanisms with microscopic NSAIDs.

In accordance with some embodiments, the dry powder administration of the NSAID, such as a salicylate like acetylsalicylic acid, can comprise particles having a median aerodynamic diameter of from about 1 µm to about 5 µm, as discussed above. The particles can be highly porous and demonstrate a sponge-like morphology or be a component of a carrier particle. The particles can also demonstrate a spheroidal shape, by which the shape and porous surface can serve to decrease the area of contact between particles, thereby leading to less particle agglomeration and more effective distribution throughout the lung. Dry powder technologies, such as PulmoSphere®, may be implemented in embodiments of the methods and systems disclosed herein.

Referring to FIG. 1, in a dry powder inhalation technique, a patient can use a dry powder inhaler 10 to inhale a powder formulation of a drug, such as a NSAID. The dose is effective to reduce a risk of a thromboembolic event in the patient. An aspect of some embodiments is the realization that because the lung is an efficient filter, it generally only permits particles having a size of less than 5 μm. For example, after the drug enters the main stem bronchus 20, the drug will enter each lung 22, 24. The drug can then pass through the bronchial trees 26, 28 until reaching the individual alveoli 30 in the lungs 22, 24, which are exceedingly numerous, as discussed below. Thus, the dry powder inhaler 10 can allow the patient to self administer a dosage of particles having a size of from about 1 μm and about 5 μm. In some embodiments, the particle size can be from about 2 μm to about 4 μm.

According to some embodiments, various types of inhalers can be used to provide the drug using a DPI or MDI delivery system. The dose administered can be effective to reduce a risk of a thromboembolic event in a patient.

For example, the dry powder inhaler 10 can comprise a mouthpiece, a reservoir for receiving the NSAID, and an actuation member for making available the NSAID for inhalation by a patient through the mouthpiece.

For example, FIGS. 2A-2F illustrate a DPI delivery device 100 having a mouthpiece 102 and a drug compartment 104. The drug compartment 104 can be inserted into an inhaler body cavity 110.

For example, as shown in FIG. 2B, the drug compartment 104 can be inserted into the body cavity 110 into a stowed position 120 for storage purposes. However, the drug compartment 104 can also be moved to a first position 122, shown in FIG. 2C, in which a first receptacle 140 of the drug compartment 104 is aligned with a mouthpiece airway 142. In this first position 122, the drug contained in the first receptacle 140 can be delivered through the mouthpiece airway 142 to be inhaled by the patient, as illustrated in FIG. 2D.

Additionally, as shown in FIG. 2E, the drug compartment 104 can be moved to a second position 124 in which a second receptacle 144 is aligned with the mouthpiece airway 142. In this position, the drug contained in the second receptacle 144 can be inhaled by the patient, as illustrated in FIG. 2F.

In the process of breathing, the lungs are normally continuously exposed to materials present in the environment of a variety of sizes. This can include pollens (20-90 μm), bacteria (0.2-200 μm), and smoke particulates (0.01-1 μm). Deposition of a particular particle depends on a number of factors, including the size and density of the particle, as well as the velocity of flow of air into and out of the lungs, and the resident time of the particle in the respiratory system. Moreover, the human body has developed systems to protect against adverse effects of some of these inhaled substances, including such processes as phagocytosis. Thus, one factor to consider when designing systems and methods for delivering a pharmaceutical compound via inhalation is the effect that particle size has on the location in the respiratory tract where drug particles are likely to become deposited after inhalation.

Particles that enter the lungs are deposited along the course of the respiratory tract by impaction, sedimentation and diffusion. Often, the behavior of particles within an airflow stream can be described by aerodynamic diameter, as described in detail herein Like the Reynold's number concept in aerodynamics, two particles having the same aerodynamic diameter will behave fundamentally the same in an airflow, regardless of their actual geometric (i.e., physical) size.

Previously it has been shown that particle size, or more accurately, aerodynamic diameter, significantly affects the location within the respiratory system where particles are most likely to become deposited after inspiration. For example, Heyder et al. (J. Aerosol. Sci. 17, 811-825, 1986) examined deposition of particles ranging in size from 5 nm to 15 μm in the respiratory tract. Their studies indicated that particles with an aerodynamic diameter greater than 5 μm deposit predominantly by inertial impaction in the mouth and upper airways. Smaller particles, (aerodynamic diameter ranging from 1-5 μm) deposit deeper in the lungs by impaction and sedimentation, while very small particles (aerodynamic diameter<1 μm), mainly remain suspended in the airflow and are exhaled.

Others have obtained similar results, suggesting that for delivery of drugs to the lungs, particles with a median aerodynamic diameter of about 2 μm are likely to be efficiently deposited in the alveolar spaces, with fractional deposition approaching 90% of the delivered particle dose (Byron, 1986, J. Pharm. Sci. 75(5), 433-438). In contrast, where particles have a median aerodynamic diameter ranging from 5-10 μm, only about 10% of the delivered dose will deposit in the alveoli, with about 40% depositing in the airways, and the remainder in the oral cavity and pharynx. Where median aerodynamic diameter is 15 μm or greater, particles deposit predominantly in the oral cavity and pharynx. Given the proximity of the alveolar epithelium to the systemic circulation, and the known benefit of delivering drugs to the lungs in order to avoid loss of a pharmaceutical agent through hydrolysis in the gut, or first pass effects due to processing in the liver, there is thus an advantage gained by designing a powdered drug composition that will be most effectively delivered to and deposited in the respiratory tract, and in particular the alveolar spaces.

Further advantages are gained by deposition of drugs in the alveolar spaces. For example, their large effective surface area spaces, and the reduced thickness of the alveolar epithelium, provides nearly immediate transfer of a drug to the circulatory system. Similarly, as the blood leaving the alveolar capillaries first travels back to the heart via the pulmonary vein, significant levels of a therapeutic molecule can be achieved in the vicinity of the heart nearly immediately. This is a particular advantage in designing treatments for cardiovascular conditions as in the present case.

Thus, an anti-thromboembolic agent such as an NSAID can be delivered at a higher plasma concentration than would otherwise be possible with an equivalent amount of an orally administered dose of the agent, and these levels can be achieved more rapidly by delivery to the lungs as compared to oral administration. Thus, those of skill in the art will appreciate that it will be possible to achieve circulating plasma levels of an NSAID in the coronary circulation effective to reduce the risk of a thromboembolic event, with a lower administered dosage than would be required if the NSAID were taken orally as per the current recommendation of physicians.

As described herein, one aspect of the subject technology provides an apparatus and method for providing a therapeutically effective dose of an NSAID in order to reduce the risk of a thromboembolic event. As discussed above, the general approach is to deliver an NSAID in a pharmaceutically acceptable powdered form (e.g., Acetylsalicylic acid, and/or derivatives thereof "ASA"; "aspirin") by means of an inhaler. However, there are a number of challenges in delivering therapeutically effective amounts of an NSAID by a dry powder inhalation system.

One challenge in designing such treatment system is the limit in terms of the size of the dose that can be comfortably tolerated by the patient. For example, in some cases, it has been shown that about 40 to about 50 mg of powdered compound can be comfortably delivered in a single inhaled dose. Coincidentally, no currently available inhaler apparatus is capable of delivering more than about 50 mg of a powder per delivery. However, the recommended dosage for ASA in order to treat suspected symptoms consistent with impending myocardial infarct are to chew two 81 mg tablets of ASA. Thus, the recommended dose for such treatment is about 160 mg. This suggests that in order to provide the identical amount of ASA as recommended by oral administration, a patient may have to take as many as four inhaled doses within the same time period. Studies have shown that patients can realistically take five inhaled doses within one minute, using currently available inhaler technology.

As discussed above, there is a general trend that deposition of particle in the alveolar spaces increases as particle size is reduced. Studies on nanoparticle distribution have shown that inhaled nanoparticles having a size <100 nm are desirable for alveolar deposition as well as for minimizing lung phagocytosis (Hoet et al., 2004, J. Nanbiotechnol. 2, doi: 10.1186/1477-3155-2-12). Nanoparticles provide additional advantages in terms of dispersion of the active compound and ultimately in the rate of uptake as compared to coarser preparations, the most obvious of which is that smaller particles tend to disperse and solubilize faster than larger ones. However, particles of nanometer size are not optimal for use in the delivery of a powdered pharmaceutical, as they tend not to deposit efficiently, but remain suspended in the airflow and are expelled upon exhalation.

One way in which to overcome this problem is through the use of methods to produce particles comprising aggregates of nanoparticles having optimal average aerodynamic size for efficient alveolar deposition. For example, Hadinoto et al. (2004, Int. J. Pharma., doi: 10.1016/j.ijpharm.2007.03.035) have shown that large hollow shells comprising nanoparticles can be produced by a spray-drying method. While these particles have a large geometric diameter (10-15 μm), they have a small aerodynamic diameter (1-3 μm) that is desirable for delivery of compounds to deeper regions of the lungs. Moreover, these large hollow shells rapidly disaggregate into the constituent nanoparticles providing rapid release of the pharmaceutical agent. In addition, Hadinoto et al. have shown that this method is adaptable to producing preparations of ASA for used in powder inhaler devices. Thus, using these methods in combination with subject technology it is possible to achieve ASA particles of an aerodynamic size for deposition to alveolar spaces, and where over 90% of the drug is released from the particles within 30 minutes.

However, despite the ability to make particles of an optimal size, there is an additional problem in preparing pharmaceutical compositions for use via inhalation. Typically, it has been observed that powders of uniform size, tend to clump and form larger aggregates via a phenomenon known as bridging. Particle when bridged behave aerodynamically as much larger particles, and as discussed above, will tend not to reach the alveolar spaces, which are desired for optimum rapid delivery of the drug of interest. In order to reduce aggregation of the pharmaceutically active agent, drugs are often blended with excipient particles such as lactose for example in order to inhibit aggregation. While the addition of excipients is an effective method to inhibit aggregation, their addition reduces the amount of the pharmaceutically active compound per measured inhaled dose. The result would be that a patient would have to take a greater number of doses in order to achieve the same intake of the pharmaceutically active compound. In an emergency situation, this may be impractical. For example, if a preparation were made that was 50% ASA ingredient and 50% excipient, with a limit of 40 mg of powder per dose, a person would have to inhale about 8 doses in order to take the recommended 162 mg of ASA for treatment of symptom suggestive of an impending infarct. Such a situation may make dry powder inhalers less practical.

However, in the present case, the inventors have now discovered that mixing particles of the same active ingredient (e.g., ASA), using batches of particles having different size distributions, can reduce bridging. For example, while a composition having a relatively uniform particle size will aggregate, providing a blended composition having some particles with a median aerodynamic diameter in a range from about 1 μm to about 5 μm, other particles with a median aerodynamic diameter in a range from about 5 μm to about 15 μm, and still other particles with a median aerodynamic diameter greater than about 15 μm, will inhibit aggregation and maintain the deposition characteristics of the preparation. In effect, the pharmaceutically active compound is used to replace the function of an excipient (such as lactose) with respect to preventing aggregation during storage of the medicament. To the knowledge of the inventor, no one has considered using the pharmaceutically active ingredient as its own excipient for the purposes of inhibiting aggregation.

In addition, and unlike many other drugs, NSAIDs, and in particular ASA, are able to enter the circulatory system effectively through routes other than through the epithelium of the alveoli. Notably, ASA is able to enter the body by absorption through the mucosal layers of the oral cavity, as well as the pharynx and undoubtedly the epithelium of the airways. Thus, regardless of particle size, it will be appreciated that by providing an inhalable form of ASA, the inhaled dosage can be substantially taken up into the systemic circulation, and be effective to reduce the risk of a thromboembolic event.

In addition, by selecting the proportions of the various particle sizes, one can provide formulations that are faster or slower acting, based on the location of where the drug is ultimately deposited. For example, in some embodiments it may be desirable to provide a preparation that comprises 80% ASA particles with a median aerodynamic diameter of about 1 μm to about 5 μm, and about 20% of particles with a median aerodynamic diameter of at least 15 μm. Other combinations are possible as well, and those of skill in the art will readily appreciate that faster acting preparations will comprise proportionately more smaller particles, while slower acting preparations will comprise proportionately more large particles. Thus, using the apparatus and methods described herein it is therefore possible to provide a therapeutically effective dose of an NSAID such as ASA via the respiratory tract, at least as rapidly as can be achieved by oral dosing.

Where a slower acting dosage form was desired, the formulation could include increasing fractions of particles with a median aerodynamic diameter in the range from about 5 μm to about 10 μm, or 15 μm or greater. These preparations would result in deposition in either the airways or oral cavity and pharynx and thus provide a more gradual increase in circulating levels of ASA and its metabolic derivatives.

In either case, the subject technology provides formulations that can deliver ASA and its pharmacologically active metabolic byproducts (e.g., salicylate) to the systemic circulation at least as quickly if not more quickly than can be accomplished via oral administration. In addition, the present formulations are effective to deliver ASA and its pharmacologically active metabolic byproducts to the systemic circulation at levels at least equal to that observed after oral administration of an equivalent dose of ASA.

For example, pharmacokinetic studies show that after oral administration of ASA peak plasma levels are achieved after about 20 minutes, after which they rapidly decline due to the relatively short elimination half-life (15-20 minutes). By comparison, plasma levels of the primary pharmacologically active metabolite salicylate, increase for a period of about 45 minutes following administration of ASA, and remain elevated for much longer due to its significantly longer elimination half-life (2-3 hr) (Dressman et al., 2012, Biowaiver Monograph for Immediate-Release Solid Oral Dosage Forms: Acetylsalicylic Acid, doi 10.1002/jps.2312).

Significantly, the pharmacokinetic behavior of ASA has been found to be linear over a dosage range from 30-400 mg. Extrapolating from these data, one would therefore expect that peak circulating plasma levels of ASA and SA would be approximately 4 mcg/mL and 10 mcg/mL respectively and with the same temporal kinetics as discussed above.

Accordingly, one aspect of the subject technology provides a dry powder that comprises a mixture of particles of various sizes.

For example, the dry powder can comprise particles of large sizes, as measured by VMGD (e.g., VMGD≥15 μm, such as ≥20 μm or 20-30 μm) and of small sizes, measured by VMGD (e.g., VMGD≤5 μm, such as 1-3 μm) at a ratio (w:w) of: about 1:1, about 1:2, about 1:3, about 1:4, about 1:5, about 1:6, about 1:7, about 1:8, about 1:10, about 1:15, about 1:20, about 1:25, about 1:30, about 1:40, about 1:50, about 1:100, about 2:1, about 3:1, about 4:1, about 5:1, about 6:1, about 7:1, about 8:1, about 9:1, about 10:1, about 15:1, about 20:1, about 25:1, about 30:1, about 40:1, about 50:1, or about 100:1, etc.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of about 10 μm or less, preferably about 5 μm or less. Particles of 10 μm or less generally can reach lungs, and particles of 5 μm or less (e.g., 1-3 μm) generally can reach alveoli.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of between about 5 μm to about 20 μm, preferably between about 5 μm to about 15 μm, or between about 5 μm to about 10 μm.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of about 15 μm or more, preferably 20 μm or more.

The above features can be combined. For example, the dry power can comprise about 50% of particles of about 5 μm or less (VMGD), about 25% of particles of about 5 to about 15 μm (VMGD), and about 25% of particles of about 15 μm or more (VMGD).

The dry powder can also comprise a mixture of particles having various mass median aerodynamic diameters (MMAD). For example, the dry powder can comprise particles of large sizes (e.g., MMAD≥15 μm, such as ≥20 μm or 20-30 μm) and of small sizes (e.g., MMAD≤5 μm, such as 1-3 μm) at a ratio (w:w) of: about 1:1, about 1:2, about 1:3, about 1:4, about 1:5, about 1:6, about 1:7, about 1:8, about 1:10, about 1:15, about 1:20, about 1:25, about 1:30, about 1:40, about 1:50, about 1:100, about 2:1, about 3:1, about 4:1, about 5:1, about 6:1, about 7:1, about 8:1, about 9:1, about 10:1, about 15:1, about 20:1, about 25:1, about 30:1, about 40:1, about 50:1, or about 100:1, etc Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of about 10 μm or less, preferably about 5 μm or less. Particles of 10 μm or less generally can reach lungs, and particles of 5 μm or less (e.g., 1-3 μm) generally can reach alveoli.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of between about 5 μm to about 20

μm, preferably between about 5 μm to about 15 μm, or between about 5 μm to about 10 μm.

Alternatively or in addition, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of about 15 μm or more, preferably 20 μm or more.

The above features can be combined. For example, the dry power can comprise about 50% of particles of about 5 μm or less (MMAD), about 25% of particles of about 5 to about 15 μm (MMAD), and about 25% of particles of about 15 μm or more (MMAD).

In some embodiments, the dry powder does not comprise, or does not substantially comprise, an excipient. In some embodiments, the dry powder does not comprise, or does not substantially comprise, an anti-aggregation (or anti-bridging) excipient.

In certain embodiments, the dry powder comprises a mixture of particles of various sizes, and is effective to substantially prevent or reduce particle bridging. In certain embodiments, at least about 40%, at least about 45%, at least about 50%, at least about 55%, at least about 60%, at least about 65%, at least about 70%, at least about 75%, at least 80%, at least about 85%, or at least about 90% of the NSAID (such as acetylsalicylic acid) in the dry powder is delivered to the alveolar spaces of a lung.

6. METHODS FOR PREPARING DRY POWDERS AND DRY PARTICLES

The respirable dry particles and dry powders can be prepared using any suitable method. Many suitable methods for preparing respirable dry powders and particles are conventional in the art, and include single and double emulsion solvent evaporation, spray drying, milling (e.g., jet milling), blending, solvent extraction, solvent evaporation, phase separation, simple and complex coacervation, interfacial polymerization, suitable methods that involve the use of supercritical carbon dioxide ($CO_2$), and other suitable methods. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

Spray Drying

Inhalable dry particles can be produced by spray drying. Suitable spray drying techniques are described, for example, by K. Masters in "*Spray Drying Handbook*", John Wiley & Sons, New York (1984); and spray drying techniques developed by BUCHI Laboratory Equipment or GEA Niro drying technology. Generally, during spray drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by Niro, Inc. (Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 100° C. to about 300° C., and preferably is about 220° C. to about 285° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the subject technology, generally, a solution, emulsion or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feedstock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer.

In one example, respirable dry particles that comprise acetylsalicylic acid can be prepared by spray drying. Spray drying is a commonly used method of drying a liquid feed through a hot gas. It is a method whereby solutions or slurries can be rapidly dried to particulate form by atomizing the liquid in a heated chamber. Typically, the hot gas can be air although when preparing chemically sensitive materials such as pharmaceuticals, and where solvents such as ethanol are used, and oxygen-free atmosphere is required and so nitrogen task will typically be used. Spray drying is frequently used in the food preparation industry and has become an important method for the dehydration of fluid foods such as milk, coffee, and egg powder. The process is also adaptable to preparations of pharmaceutical and chemical formulations.

The liquid feed varies depending on the material being dried and is not limited to food or pharmaceutical products, and may be a solution, colloid or suspension. The process is a one step rapid method that typically eliminates additional processing. By controlling process conditions particles of the desired size can be reproducibly formed. In some cases, excipients can be included with the active pharmaceutical ingredient such that a complex particle of API and excipient can be produced in a single step process. In other cases, an active pharmaceutical particulate preparation can be produced in a first spray-drying process, and that product then modified by the subsequent addition of one or more pharmaceutically acceptable excipients. In some cases it is possible to add excipients by a subsequent spray-drying process.

In some spray-drying methods the liquid feed is pumped through an atomizer nozzle, or array of nozzles, that produce fine droplets that are introduced into the main drying chamber. Atomizers can vary there being rotary, single fluid, two-fluid, and ultrasonic designs. These different designs provide a variety of advantages, applicability and disadvantages depending on the particular spray drying process required. The hot drying gas can be passed as a concurrent or counter-current flow to the atomizer direction. The concurrent flow enables the particles to have a lower residence time within the system and the particle separator thus operates more efficiently. In some systems the particle separator is a cyclone device. The counter-current flow method enables a greater residence time of the particles in the chamber. Therefore, in general a spray-drying method will consist of the steps of pre-concentration of liquid, atomization, drying in a hot gas atmosphere, separation of the dried powder from moist gas, cooling, and then packaging of the finished product.

In one embodiment of the present invention, feed solutions with aspirin concentrations of either 2% w/w, or 5% w/w, were prepared by adding aspirin to the appropriate solvent followed by stirring until a homogeneous solution was obtained. A BUCHI spray dryer model B-290 Advanced was used in all experiments. The unit was equipped with a two fluid nozzle where the nozzle and diameter were 1.4 mm and 0.7 mm, respectively. To high-performance cyclones were used to collect the dried product. The spray-drying unit was operated in open cycle, with the aspirator blowing nitrogen at 100% of capacity, corresponding to a flow rate of the dry nitrogen of approximately 40 kg per hour. The flow rate of atomization nitrogen was adjusted to 40 mm or 50 mm in the rotameter, depending on the particular trial. Before feeding the stock solution, the spray dryer was stabilized the solvent. During the stabilization period, the solvent flow rate was adjusted in order to give the target outlet temperature. After stabilization of the outlet temperature, the feed of the spray dryer was commuted from the solvent to the product solution (inlet temperature was then readjusted to maintain the outlet temperature in the target value). At the end of the stock solution, the feed was once more commuted to solvent, in order to rinse the feed line and carry out a controlled shutdown.

The initial objective of these experiments was to isolate the amorphous form of aspirin, in order to fully characterize it. However, as was discovered from a review of the literature, aspirin presents a negative Tg (of −30° C.), and as such the option of producing a crystalline size reduced active pharmaceutical with this technique was attempted. For that purpose, for solutions of aspirin in ethanol (the most suited solvent to dissolve the aspirin, given its high solubility and its approval for inhalation use) were prepared and spray dried as follows. Inlet temperature ranged from about 80° C. to about 160° C. Outlet temperature was initially set to 65° C. In one experiment the outlet temperature was increased to 100° C. in an attempt to accelerate the amorphous-crystalline conversion, in the hopes that this would reduce losses that are typical of the transient glassy state of the material. However, increasing the outlet temperature did not produce any appreciable increase in overall yield of product. The rotameter was varied from about 40 mm to about 50 mm. Feed rate was typically about 5 mL per minute. Following spray drying, a number of analytical methods were used to evaluate the resulting product.

X-ray powder diffraction (XRPD) showed that in each of the four different batches prepared aspirin appeared to be crystalline in form, and the diffractogram was similar to that of the starting material. In addition, the spray dried products presented thermal grams that were identical to the input material.

In some cases overall yield ranged from about 55% to about 65%. Without being bound to a particular theory it is expected that this is likely related to the occurrence of crystallization during the spray drying process since it is expected that the product must undergo a glassy state, which will typically promote adherence and therefore loses a product to the walls of the spray dryer apparatus itself.

The melting temperature of the resulting spray dried product ranged from about 133° C. to about 137° C., comparing favorably with the published melting point for aspirin (136° C.). A measure of hygroscopic properties showed await change ranging from −0.4% to about 1.2% when the products were exposed to an atmosphere with 95% relative humidity. These results suggest no issues with hygroscopic behavior and that with respect to this property, spray dried aspirin behaves in a manner similar to that of unprocessed aspirin.

Particle size distribution analysis showed that $DV_{10}$ ranged from about 0.9 μm to about 1.2 μm, $DV_{50}$ ranged from about 3 μm to about 6 μm, and $DV_{90}$ ranged from about 8 μm to about 24 μm. It was discovered that by reducing feed concentration of aspirin to 2% w/w, a smaller average particle size could be obtained, which was within typical inhalation range.

HPLC analysis showed aspirin purity to range from about 92% to about 98%, with the major "impurity" being salicylic acid, which ranged from about 0.3% to about 0.5%. Residual solvent ranged from about 90 ppm to about 150 ppm, well below the limits defined in the ICH Q3A guidelines.

The feedstock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions (such as phosphate buffer).

The feedstock or components of the feed stock can have any desired pH, viscosity or other properties. If desired, a pH buffer can be added to the solvent or co-solvent or to the formed mixture. Generally, the pH of the mixture ranges from about 3 to about 8.

Jet Milling

Respirable particles can also be produced by jet-milling. See, e.g., techniques developed by Apex Process Technology or Jetpharma SA. Jet milling is a process of using highly compressed air or other gasses, usually in a vortex motion, to impact fine particles against each other in a chamber. Jet mills are capable of reducing solids to particle sizes in the low-micron to submicron range. The grinding energy is created by gas streams from horizontal grinding air nozzles. Particles in the fluidized bed created by the gas streams are accelerated towards the center of the mill, colliding with slower moving particles. The gas streams and the particles carried in them create a violent turbulence and as the particles collide with one another they are pulverized.

In some embodiments, jet-milling was able to produce aspirin particles with a FPF within the desired inhalable range for maximal deposition at the deepest levels of the lung. In some cases the $DV_{90}$ was less than about 9 μm, in some cases less than about 5 μm, and in some cases less than about 3 μm. Particles produced by jet milling can be efficiently and predictably delivered from a dry powder inhaler device, and at least 25% of the particles are of a size that would be expected to deposit within the alveolar spaces of the lungs. In some cases at least 50% of the particles are of a size that would be expected to deposit within the alveolar spaces of the lungs. In some cases at least 75% of the particles are of a size that would be expected to deposit within the alveolar spaces of the lungs. In some cases at least 90% of the particles are of a size that would be expected to deposit within the alveolar spaces of the lungs.

Wet Polishing

Wet polishing is a process that combines a technology to attain a small particle size (either a bottom up technique such as controlled crystallization or nanocrystallization or top down technique such as high shear mixing or high pressure homogenization) with a suitable isolation technology (for example spray drying or filtration with a drying process). See, e.g., techniques developed by Hovione. These combinations can be used to tune the particle size and morphology to meet specific drug delivery needs. The method allows control of particle size distribution with tight spans and in-process sampling, and maintains crystalline state (little or no amorphous content).

Wet polishing technique can be repeated multiple times to achieve a particular size of about 500 nanometers or less. Studies were undertaken to investigate whether wet polishing could provide an appropriate method for producing aspirin particles of an inhalable size and which were deliverable from a dry powder inhaler device. Initially, a literature review was conducted in order to determine the best candidate anti-solvent for use in reducing aspirin particle size by a wet-polishing method. Solvents were evaluated by their predicted ability with respect to minimal solubility of aspirin. From this review, the following candidate solvents were identified: water, benzene, toluene, hexane, n-heptane, dibutyl ether and di-isopropyl-ether.

After considering a number of factors in the end it was determined that only n-heptane and toluene fulfilled all the requirements, and therefore these were selected for further evaluation. Suspensions of aspirin at 5% w/w were prepared with the various anti-solvents, by charging the required amount of anti-solvent, charging the required amount of aspirin, and then stirring until a homogeneous suspension was obtained. The suspensions were qualitatively evaluated at room temperature and then filtered using a 0.45 μm membrane, which was then placed in an oven and dried at 60° C. until the solvent had completely evaporated. A quantitative analysis was performed on the residue that remained in the membrane by weighing the membrane before and after the test. From this analysis it was determined that aspirin was partially soluble in toluene, and displayed a phobic behavior towards n-heptane.

Suspensions were prepared using either toluene or n-heptane at an aspirin concentration of 5% w/w. Each individual suspension was then subjected to a milling operation using a Microfluidics Model M-110EH-30 apparatus. Milling was conducted at a pressure of 50 bar using a 200 μm chamber for between 20 and 70 cycles. Input temperatures ranged from about 80° C. to about 140° C. Output temperatures ranged from about 65° C. to about 90° C. The process yield ranged from about 5% to about 25%.

Analysis of the resulting product revealed a $DV_{10}$ ranging from about 1.5 μm to about 3.3 μm, $DV_{50}$ ranging from about 3.3 μm to about 6.7 μm, and $DV_{90}$ ranging from about 6.3 μm to about 12.0 μm. HPLC assay of the final product revealed a composition of aspirin ranging from 90% to about 98%, with impurities ranging from about 1.4% to about 12%. The primary impurity was salicylic acid. It was also observed that all of the products obtained by wet polishing were more hygroscopic than the raw material, showing a water gain of about 5% when in the presence of 95% relative humidity.

In addition, when tested for aerodynamic performance, aspirin processed by wet polishing performed poorly in two different dry powder delivery devices. When examining devices loaded with either 15 mg or 40 mg, a significant amount of material (about 25 to 30%) was retained within the inhalation device itself. Overall, the results suggested that wet polishing alone impacts to a significant extent the physical and chemical properties of aspirin, and therefore were seen to be less desirable for producing a pharmaceutical product for inhalation. Wet polishing may nonetheless be a suitable method for micronization of aspirin for other purposes.

Controlled Crystallization

In some cases it is possible to produce aspirin particles of a desired size using a process known as controlled crystallization. It is well known in the art that the crystalline state of most compounds is more thermodynamically stable that the amorphous state. As a result, producing aspirin in crystalline form is expected to improve stability of the active ingredient. In addition, production of aspirin in crystalline form also provides the potential to modify the active ingredient to optimize various biochemical properties, such as solubility, dissolution rate and pH solubility profile (among others) in order to improve pharmacokinetic performance. In some cases, sequential crystallization steps can be used to improve the purity of the active ingredient and selectively remove undesirable impurities.

Similarly, through the proper selection of various solvents and anti-solvents, it is possible to manipulate physical characteristics such as crystal shape. It is well known that certain crystal shapes are difficult to handle both at the product development and manufacturing stages. For example, needles and flakes are widely regards as less desirable particle shapes. It is possible however, to manipulate crystal formation in order to direct the final product to more suitable crystal shapes. In some cases, it is possible to grow crystals with high aspect ratios using non-polar hydrocarbon solvents such as hexane or heptane. In contrast, crystals having a low aspect ratio can be produced using polar solvents such as methanol or ethanol. The addition of surface active "impurities" can also be used to inhibit crystal growth in certain planar forms.

The solubility of aspirin in a number of solvents was first evaluated prior to initiating controlled crystallization by addition of a suitable anti-solvent. The results are shown in the following Table 2.

TABLE 2

Solubility of aspirin

| Solvent | T (° C.) | g/ml | T (° C.) | g/ml |
|---------|----------|-------|----------|-------|
| EtOH    | 23       | 0.125 | 3        | 0.063 |
| Acetone | 23       | 0.200 | 3        | 0.143 |
| MeOH    | 23       | 0.167 | 3        | 0.133 |
| DMF     | 23       | 0.500 | —        | —     |
| THF     | 23       | 0.500 | 3        | 0.250 |
| PEG-200 | 23       | 0.077 | —        | —     |

Next, several small crystallization experiments were carried out to evaluate the behavior of the acetylsalicylic acid in different systems. Each experiment consisted of dissolving 2 gm of aspirin in a solvent (T=20-25° C.), and then adding this solution to the anti-solvent (100 vol. of anti-solvent at ~5° C.). The suspension obtained was stirred for 15 min and solid material collected by filtration and then dried. Table 3 summarizes the conditions of each experiment

TABLE 3

Summary of the crystallization experiments

| Solvent | (v/w) | T (° C.) | Anti-Solvent | (v/w) | T (° C.) | Crystals | Yield |
|---------|-------|----------|--------------|-------|----------|----------|-------|
| EtOH    | 8     | 20-25    | H$_2$O       | 100   | 4        | yes      | 51.5  |
| EtOH    | 8     | 20-25    | n-Hept       | 100   | 4        | yes      | 58.0  |
| EtOH    | 8     | 20-25    | Toluene      | 100   | 4        | no       | —     |
| EtOH    | 8     | 20-25    | H$_2$O       | 100   | 4        | yes      | 53.0  |
| H2SO4   | 0.05  |          |              |       |          |          |       |
| THF     | 2.5   | 20-25    | H$_2$O       | 100   | 4        | yes      | 53.5  |
| THF     | 2.5   | 20-25    | Toluene      | 100   | 4        | yes      | 45.5  |
| THF     | 2.5   | 20-25    | n-Hept       | 100   | 4        | yes      | 89.0  |
| MeOH    | 6     | 20-25    | H$_2$O       | 100   | 4        | yes      | 64.5  |
| MeOH    | 6     | 20-25    | n-Hept       | 100   | 4        | yes      | 17.0  |
| MeOH    | 6     | 20-25    | Toluene      | 100   | 4        | no       | —     |
| Acetone | 7     | 20-25    | H$_2$O       | 100   | 3        | yes      | 43.0  |
| Acetone | 7     | 20-25    | n-Hept       | 100   | 4        | yes      | 71.5  |
| Acetone | 7     | 20-25    | Toluene      | 100   | 4        | yes      | 34.5  |

Excipients

Particles described herein can be encapsulated, e.g., by a pharmaceutical excipient such as lactose, sugar, or a polymer.

In addition, particles described herein can be mixed and/or coated with various pharmaceutically acceptable excipients. Excipients can be included in order to improve aerodynamic performance of the active drug, to improve bioavailability, increase stability, to modulate pH, to provide sustained release properties, to provide taste-masking of an irritating drug and/or to improve pharmacokinetic performance. In one embodiment, a dry powder comprises an amount of excipient effective to provide taste-masking of an irritating drug. In terms of suitable formulations for inhalation, not only is particle size important in order to reach a desired region of the respiratory system, but the formulation must be acceptable to patients. In early aspects of the studies involved in the present invention, it was discovered that pure aspirin is quite irritating to the respiratory system and thus unlikely to be acceptable to users. Consequently, it became necessary to find a suitable excipient in order to mask this property of aspirin.

With dry powder formulations, excipients can also provide a carrier function to reduce clumping of the active pharmaceutical ingredient and to improve suspension of the formulation in the airflow as the pharmaceutical preparation is being inhaled. Such carriers can include substances such as, but not limited to, sugars/sugar alcohols such as glucose, saccharose, lactose and fructose, starches or starch derivatives, oligosaccharides such as dextrins, cyclodextrins and their derivatives, polyvinylpyrrolidine, alginic acid, tylose, silicic acid, cellulose, cellulose derivatives, sugar alcohols such as mannitol or sorbitol, calcium carbonate, calcium phosphate, lactose, lactitol, dextrates, dextrose, maltodextrin, saccharides including monosaccharides, disaccharides, polysaccharides; sugar alcohols such as arabinose, ribose, mannose, sucrose, trehelose, maltose and dextran.

In some cases, an excipient can be provided in order to coat the active pharmaceutical ingredient, thus "masking" it. Masking is especially useful when the unmodified active pharmaceutical is irritating or otherwise unpleasant to the recipient. For example, in some cases it has been shown that coating a bitter molecule with a hydrogenated oil and surfactant combination is effective to cover the otherwise unpleasant taste of the active ingredient. For example, an excipient, e.g., DPPC and DSPC can be used in an amount effective to mask the taste of a bitter or unpleasant tasting API. One such excipient, discovered as part of the current studies to be useful in reducing aspirin irritation upon inhalation, are zwitterionic phospholipids, including surfactant compounds. Examples of suitable phospholipid excipients include, without limitation, phosphatidylcholines, phosphatidylethanolamines, phosphatidylinositol, phosphatidylserines, sphingomyelin or other ceramides, as well as phospholipid containing oils such as lecithin oils. Combinations of phospholipids, or mixtures of a phospholipid(s) and other substance(s), may be used. In one embodiment, the phospholipid used as excipient is soy lecithin. In another embodiment, the phospholipid is endogenous to the lung. The excipient may be effective to suppress coughing or bronchospasm that occurs upon inhalation of aspirin.

Non-limiting examples of the phospholipids that may be used in the present composition include, dipalmitoylphosphatidylcholine (DPPC), distearoylphosphatidylcholine (DSPC), dilaurylolyphosphatidylcholine (DLPC), dimyristoylphosphatidylcholine (DMPC), dioleoylphosphatidylcholine (DOPC), dilaurylolylphosphatidylglycerol (DLPG), dimyristoylphosphatidylglycerol (DMPG), dipalmitoylphosphatidylglycerol (DPPG), distearoylphosphatidylglycerol (DSPG), dioleoylphosphatidylglycerol (DOPG), dimyristoyl phosphatidic acid (DMPA), dimyristoyl phosphatidic acid (DMPA), dipalmitoyl phosphatidic acid (DPPA), dipalmitoyl phosphatidic acid (DPPA), dimyristoyl phosphatidylethanolamine (DMPE), dipalmitoyl phosphatidylethanolamine (DPPE), dimyristoyl phosphatidylserine (DMPS), dipalmitoyl phosphatidylserine (DPPS), dipalmitoyl sphingomyelin (DPSP), and distearoyl sphingomyelin (DSSP).

In one embodiment, dipalmitoyl phosphatidylcholine (DPPC), distearoyl phosphatidylcholine (DSPC) or a mixture thereof are used as an excipient. For example, DPPC and DSPC are natural constituents of pulmonary surfactant. Pulmonary surfactant is a surface-active lipoprotein complex produced by type II alveolar cells. The proteins and lipids that make up the surfactant have a hydrophilic region and a hydrophobic region. By adsorbing to the air-water interface of alveoli with the hydrophilic head groups in the water and the hydrophobic tails facing towards the airspace, surfactants are effective to reduce surface tension to near-zero levels and permit expansion of the lung with less force than would otherwise be required. Consequently, pulmonary surfactant, by reducing surface tension, allows the lung to inflate much more easily, thus reducing the effort required to inflate the lungs.

An excipient (e.g., a phospholipid) may be used to mask taste, mask irritation and/or improve the aerodynamic performance of the present particles. The excipient may be any substance as described herein. The excipient(s) (e.g., phospholipids) may be present at levels ranging from about 0% to about 99% (w/w), from about 0.01% to about 80% (w/w), from about 0.05% to about 70% (w/w), from about 0.1% to about 60% (w/w), from about 0.1% to about 50% (w/w), from about 0.1% to about 40% (w/w), from about 0.1% to about 30% (w/w), from about 0.1% to about 20% (w/w), from about 0.1% to about 10% (w/w), from about 0.05% to about 8% (w/w), from about 0.1% to about 6% (w/w), from about 5% to about 10% (w/w), from about 3% to about 8% (w/w), from about 2% to about 6% (w/w), from about 0.1% to about 5% (w/w), from about 0.1% to about 4% (w/w), from about 0.1% to about 3% (w/w), from about 0.1% to about 2% (w/w), from about 0.1% to about 1% (w/w), from about 1% to about 6% (w/w), from about 1% to about 5% (w/w), from about 1% to about 4% (w/w), or from about 1% to about 3% (w/w) of the particles. In certain embodiments, one or more excipients (e.g., one or more phospholipids) are present at levels in a range from about 0.1% to about 10% (w/w), from about 1% to about 5% (w/w), about 0.1%, about 5% (w/w), about 3%, or about 10% (w/w) of the particles.

Aspirin alone may be too irritating and evoke a choking response (e.g., coughing, bronchospasms) when inhaled. In one embodiment, after coating aspirin with a surfactant, the modified formulation is well tolerated (i.e., does not evoke a choking response) when administered by inhalation either orally or nasally. Also surprising was the observation that nasally delivered surfactant coated aspirin was able to alleviate symptoms of headache and nasal congestion within seconds of administration. For example, symptoms of headache and nasal congestion may be alleviated within about 10 seconds, about 15 seconds, about 20 seconds, about 30 seconds, or within about 45 seconds. To the inventors' knowledge, this is the first demonstration that a preparation comprising aspirin and a phospholipid can provide rapid relief from headache and/or nasal congestion when delivered in this manner.

In addition, in some embodiments, the surfactant can be provided in combination with one or more additional excipients including absorbents, acidifiers, alkalizers, buffers, antimicrobial agents, antioxidants, binders, solubilizing agents, solvents, viscosity modifiers, humectants and combinations thereof. In some embodiments the formulation includes salts in amounts effective to render the dissolved formulation isosmotic with the lung.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 μm VMGD.

The diameter of the respirable dry particles, for example, their VMGD, can be measured using an electrical zone sensing instrument such as a Multisizer He, (Coulter Electronic, Luton, Beds, England), or a laser diffraction instrument such as a HELOS system (Sympatec, Princeton, N.J.). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Model 3225 Aerosizer DSP Particle Size Analyzer (Amherst Process Instrument, Inc., Amherst, Mass.) can be used to measure aerodynamic diameter. The Aerosizer measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor (ACI) and the multi-stage liquid impinger (MSLI) methods. Another method of measuring the aerodynamic diameter is with a Next Generation Impactor (NGI). The NGI operates on similar principles of inertial impaction as the ACI. The NGI consists of seven stages and can be calibrated at flow rates of 30, 60, and 100 LPM. In contrast to the ACI, for which the impactor stages are stacked, the stages of the NGI are all in one plane. Collection cups are used to collect the particles below each stage of the NGI. U.S. Pat. No. 8,614,255. The methods and instruments for measuring particle aerodynamic diameter are well known in the art.

Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopia convention, Rockville, Md., $10^{th}$ Supplement, 4950-4951, 1999.

Fine particle fraction (FPF) can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cut-offs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages of the eight-stage ACI and allows for the collection of two separate powder fractions. Specifically, a two-stage collapsed ACI is calibrated so that the fraction of powder that is collected on stage one is composed of respirable dry particles that have an aerodynamic diameter of less than 5.6 µm and greater than 3.4 µm. The fraction of powder passing stage one and depositing on a collection filter is thus composed of respirable dry particles having an aerodynamic diameter of less than 3.4 µm. The airflow at such a calibration is approximately 60 L/min. Formulation produced by the methods described herein can be effectively delivered at airflow rates ranging from about 20 L/min to about 60 L/min.

The FPF (<5.6) has been demonstrated to correlate to the fraction of the powder that is able to make it into the lung of the patient, while the FPF (<3.4) has been demonstrated to correlate to the fraction of the powder that reaches the deep lung of a patient. These correlations provide a quantitative indicator that can be used for particle optimization.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose. The FPF_TD (<5.0) is the ratio of the interpolated amount of powder depositing below 5.0 µm on the ACI to the nominal dose. The FPF_RD (<5.0) is the ratio of the interpolated amount of powder depositing below 5.0 µm on the ACI to either the gravimetric recovered dose or the analytical recovered dose.

Another way to approximate emitted dose is to determine how much powder leaves its container, e.g. capture or blister, upon actuation of a dry powder inhaler (DPI). This takes into account the percentage leaving the capsule, but does not take into account any powder depositing on the DPI. The emitted dose is the ratio of the weight of the capsule with the dose before inhaler actuation to the weight of the capsule after inhaler actuation. This measurement can also be called the capsule emmited powder mass (CEPM)

A Multi-Stage Liquid Impinger (MSLI) is another device that can be used to measure particle size distribution or fine particle fraction. The Multi-stage liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI. U.S. Pat. No. 8,614,255.

The subject technology also relates to a respirable dry powder or respirable dry particles produced using any of the methods described herein.

The respirable dry particles of the subject technology can also be characterized by the chemical stability of the salts or the excipients that the respirable dry particles comprise. The chemical stability of the constituent salts can affect important characteristics of the respirable particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC). Respirable dry particles of the subject technology include salts that are generally stable over a long period time.

If desired, the respirable dry particles and dry powders described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. The maltodextrin may act as an amorphous phase stabilizer and inhibit the components from converting from an amorphous to crystalline state. Alternatively, a post-processing step to help the particles through the crystallization process in a controlled way (e.g., on the baghouse at elevated humidity) can be employed with the resultant powder potentially being further processed to restore their dispersibility if agglomerates formed during the crystallization process, such as by passing the particles through a cyclone to break apart the agglomerates. Another possible approach is to optimize around process conditions that lead to manufacturing particles that are more crystalline and therefore more stable. Another approach is to use different excipients, or different levels of current excipients to attempt to manufacture more stable forms of the salts.

The respirable dry particles and dry powders described herein are suitable for inhalation therapies. The respirable dry particles may be fabricated with the appropriate material, surface roughness, diameter, and tap density for localized delivery to selected regions of the respiratory system such as the deep lung or upper or central airways. For example, higher density or larger respirable dry particles may be used for upper airway delivery, or a mixture of varying size respirable dry particles in a sample, provided with the same or a different formulation, may be administered to target different regions of the lung in one administration.

In order to relate the dispersion of powder at different inhalation flow rates, volumes, and from inhalers of different resistances, the energy required to perform the inhalation maneuver can be calculated. Inhalation energy can be calculated from the equation $E=R^2Q^2V$ where E is the inhalation energy in Joules, R is the inhaler resistance in $kPa^{1/2}$/LPM, Q is the steady flow rate in L/min and V is the inhaled air volume in L.

Healthy adult populations are predicted to be able to achieve inhalation energies ranging from 2.9 to 22 Joules by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa1/2/LPM, with a inhalation volume of 2 L based on both FDA guidance documents for dry powder inhalers and on the work of Tiddens et al. (Journal of Aerosol Med, 19, (4), p. 456-465, 2006) who found adults averaging 2.2 L inhaled volume through a variety of DPIs.

Dry powder particles can also be prepared using cone-jet mode of electrohydrodynamic atomization, as described by Li et al., Chemical Engineering Science 61 (2006) 3091-3097. For example, an aspirin solution flowing through a needle can be subjected to an electric field to generate droplets. The method is said to generate a near-monodispersed distribution of droplet relics, leading to form aspirin particulate crystals.

7. METHODS OF TREATMENT

In other aspects, the subject technology is a method for treating (including prophylactic treatment or reducing the risk) of a cardiovascular disease (such as thrombosis), comprising administering to the respiratory tract of a subject in need thereof an effective amount of respirable dry particles or dry powder, as described herein.

Cardiovascular diseases include, for example, atherosclerosis, coronary artery disease (CAD), angina pectoris (commonly known as "angina"), thrombosis, ischemic heart disease, coronary insufficiency, peripheral vascular disease, myocardial infarction, cerebrovascular disease (such as stroke), transient ischemic attack, arteriolosclerosis, small vessel disease, elevated cholesterol, intermittent claudication or hypertension.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, North Carolina), FlowCapss®, TwinCaps®, XCaps (Hovione, Loures, Portugal), Inhalators® (Boehringer-Ingelheim, Germany), Aerolizer® (Novartis, Switzerland), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 µl, 770 µl, 680 µl, 480 µl, 360 µl, 270 µl, and 200 µl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 6 inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, 4, 5 or 6 inhalations. The respirable dry particles and dry powders are preferably administered in a single, breath-activated step using a breath-activated DPI. When this type of device is used, the energy of the subject's inhalation both disperses the respirable dry particles and draws them into the respiratory tract.

The time between multiple inhalations may be about 15 seconds, about 30 seconds, about 45 seconds, about 1 minute, about 2 minutes, about 3 minutes, about 4 minutes, about 5 minutes, between about 15 seconds and 5 minutes, between about 30 seconds and 4 minutes, or between about 15 seconds and 4 minutes. The time between multiple inhalations may be up to about 15 seconds, up to about 30 seconds, up to about 45 seconds, up to about 1 minute, up to about 2 minutes, up to about 3 minutes, up to about 4 minutes, up to about 5 minutes, up to about between about 15 seconds and 5 minutes, up to about between about 30 seconds and 4 minutes, or up to about between about 15 seconds and 4 minutes.

The respirable dry particles or dry powders can be delivered by inhalation to a desired area within the respiratory tract, as desired. It is well known that particles with an MMAD of about 1 µm to about 3 µm, can be effectively delivered to the deep lung regions such as the alveolar spaces. Larger aerodynamic diameters, for example, from about 3 µm to about 5 µm can be delivered to the central and upper airways.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors that contribute to oral deposition of a powder include the size distribution of the individual particles and the dispersibility of the powder. If the MMAD of the individual particles is too large, e.g. above 5 µm, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of about 5 µm or less), the size distribution of the inhaled powder may have an MMAD of greater than about 5 µm, leading to enhanced oral cavity deposition.

Therefore, it is desirable to have a powder in which the particles are small (e.g., MMAD of 5 µm or less, e.g. between about 1 µm to 5 µm), and are highly dispersible (e.g. 1/4 bar or alternatively, 0.5/4 bar of 2.0, and preferably less than 1.5). More preferably, the respirable dry powder is comprised of respirable dry particles with an MMAD between 1 to 4 µm, between 1 to 3 µm, about 3 µm, about 2.9 µm, about 2.8 µm, about 2.7 µm, about 2.6 µm, about 2.5 µm, about 2.4 µm, about 2.3 µm, about 2.2 µm, about 2.1 µm, or about 2.0 µm, and have a 1/4 bar less than 1.4, or less than 1.3, and more preferably less than 1.2.

The absolute geometric diameter of the particles measured at 1 bar using the HELOS system is not critical provided that the particle's envelope density is sufficient such that the MMAD is in one of the ranges listed above, wherein MMAD is VMGD times the square root of the envelope density (MMAD=VMGD*sqrt (envelope density)). If it is desired to deliver a high unit dose of salt using a fixed volume-dosing container, then, particles of higher envelop density are desired. High envelope density allows for more mass of powder to be contained within the fixed volume-dosing container. Preferable envelope densities are greater than 0.1 g/cm$^3$, greater than 0.25 g/cm$^3$, greater than 0.4 g/cm$^3$, greater than 0.5 g/cm$^3$, and greater than 0.6 g/cm$^3$.

The respirable dry powders and particles of the subject technology can be employed in compositions suitable for drug delivery via the respiratory system. For example, such compositions can include blends of the respirable dry particles of the subject technology and one or more other dry particles or powders, such as dry particles or powders that contain another active agent, or that consist of or consist essentially of one or more pharmaceutically acceptable excipients.

Respirable dry powders and dry particles suitable for use in the methods of the subject technology can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the subject technology, most of the mass of respirable dry powders or particles deposit in the deep lung. In another embodiment of the subject technology, delivery is primarily to the central airways. In another embodiment, delivery is to the upper airways.

The respirable dry particles or dry powders of the subject technology can be delivered by inhalation at various parts of the breathing cycle (e.g., laminar flow at mid-breath). An advantage of the high dispersibility of the dry powders and dry particles of the subject technology is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they are released later in the inhalation.

The dry powders of this subject technology provide advantages for targeting the timing of drug delivery in the breathing cycle and also location in the human lung. Because the respirable dry powders of the subject technology can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate that diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Esevier, Amsterdam (1985).

Suitable intervals between doses that provide the desired therapeutic effect can be determined based on the severity of the condition, overall well-being of the subject and the subject's tolerance to respirable dry particles and dry powders and other considerations. Based on these and other considerations, a clinician can determine appropriate intervals between doses. Generally, respirable dry particles and dry powders are administered once, twice or three times a day, as needed.

In some embodiments the amount of NSAID delivered to the respiratory tract (e.g., lungs, respiratory airway) is about 0.001 mg/kg body weight/dose to about 2 mg/kg body weight/dose, about 0.002 mg/kg body weight/dose to about 2 mg/kg body weight/dose, about 0.005 mg/kg body weight/dose to about 2 mg/kg body weight/dose, about 0.01 mg/kg body weight/dose to about 2 mg/kg body weight/dose, about 0.02 mg/kg body weight/dose to about 2 mg/kg body weight/dose, about 0.05 mg/kg body weight/dose to about 2 mg/kg body weight/dose, about 0.075 mg/kg body weight/dose to about 2 mg/kg body weight/dose, about 0.1 mg/kg body weight/dose to about 2 mg/kg body weight/dose, about 0.2 mg/kg body weight/dose to about 2 mg/kg body weight/dose, about 0.5 mg/kg body weight/dose to about 2 mg/kg body weight/dose, or about 0.75 mg/kg body weight/dose to about 2 mg/kg body weight/dose.

In certain embodiments, at least about 50%, at least about 60%, at least about 70%, at least about 75%, at least about 80%, at least about 85%, at least about 90%, at least about 95%, or at least about 99%, of the administered acetylsalicylic acid reaches the systemic circulation of a subject within about 60 minutes upon administration, or within about 40 minutes upon administration, or within about 30 minutes upon administration, or within about 20 minutes upon administration, or within about 15 minutes upon administration, or within about 5 minutes upon administration.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 30 mg of acetylsalicylic acid.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 40 mg of acetylsalicylic acid.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 50 mg of acetylsalicylic acid.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 80 mg of acetylsalicylic acid.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 160 mg of acetylsalicylic acid.

The doses of acetylsalicylic acid administered in order to achieve a level (or an average level among a population of patients) that is substantially the same, or higher as compared to those delivered by oral administration of about 30 mg, about 40 mg, about 50 mg, about 80 mg, or about 160 mg of acetylsalicylic acid can be determined by conventional methods. The dosing, administration techniques and schedules are known in the art and are within the ability of the skilled clinician. For example, the serum level of acetylsalicylic acid, or a metabolite thereof, in a subject (or average serum level among a population of subjects) can be determined by conventional pharmacokinetic or pharmacodynamics studies.

In certain embodiments, the method and delivery devices described herein can deliver acetylsalicylic acid to the systemic circulation such that the circulating plasma level of acetylsalicylic acid is at least about 1 µg/mL, at least about 2 µg/mL, at least about 3 µg/mL, at least about 4 µg/mL, at least about 5 µg/mL, or at least about 6 µg/mL within about 60 minutes upon administration, or within about 40 minutes upon administration, or within about 30 minutes upon administration, or within about 20 minutes upon administration, or within about 15 minutes upon administration, or within about 5 minutes upon administration.

In certain embodiments, the method and delivery devices described herein can deliver acetylsalicylic acid to the systemic circulation such that circulating plasma level of salicylate is about 8 µg/mL, about 9 µg/mL, about 10 µg/mL, about 11 µg/mL, about 12 µg/mL, about 15 µg/mL, within about 60 minutes upon administration, or within about 40 minutes upon administration, or within about 30 minutes upon administration, or within about 20 minutes upon administration, or within about 15 minutes upon administration, or within about 5 minutes upon administration.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

The following examples of specific aspects for carrying out the present invention are offered for illustrative purposes only, and are not intended to limit the scope of the present invention in any way.

Example 1 Development of Aspirin Particles for Inhalation

This study was to develop phospholipid coated aspirin particles with particle size less than 2.0 µm for deep lung tissue delivery. This development work was carried out to achieve following target particle size: Dv50 of 0.5 nm to 2.0 µm; Dv90 of 1.5 to 2.0 µm.

Jet milling was selected as a method for micronization of aspirin particles to achieve target particle size. Jet milling operation was successfully reproduced with Dv50s of 0.4 µm and Dv90s of 1.3 µm and 1.6 µm for the two batches manufactured. Micronized particles were then spray-dried using DSPC (1,2-distearoyl-(sn)-glycero-3-phosphocholine) or soy lecithin to reduce particle agglomeration and irritation on inhalation. 79% yield for DSPC/aspirin and 54% yield for soy lecithin/aspirin were obtained.

Particle size analysis at each step was carried out. Spray-dried DSPC/aspirin particles ranged from 1.8 to 3.6 µm and lecithin/ASA particles ranged from 1.7 to 3.3 µm.

DSC studies showed no change in the crystalline structure of aspirin before and after spray-drying with DSPC. TGA showed 0.6% moisture content for both pre- and post-spray-dried particles indicating absence of any residual solvent after spray-drying.

Formulation Development

1. Acetylsalicylic Acid

Rhodine 3040 US obtained from Rhodia Inc. was used for all experiments. Particles were dispersed in 0.1% w/w docusate sodium in water and observed under a light microscope to confirm particle size. Particles ranging from 66 to 280 µm were observed confirming data from certificate of analysis, though observed "rounding" of the particulates is indicative of partial dissolution in the aqueous dispersant.

2. Particle Size Analysis

Particle size analysis was carried out using laser diffraction and light microscopy.

2.1. Laser Diffraction

Horiba LA-950 V2 with fraction cell was used for laser diffraction studies using the following parameters: dispersion media: 0.05% w/w soy lecithin dissolved in n-hexane; refractive index of media: 1.334; refractive index of ASA particles: 1.5623; i-value: 0.01. The i-value is an imaginary component that is used by the laser diffraction algorithm to account for the absorption of light by the particles. A stock dispersion of particles in the same media was prepared and added drop-wise to the fraction cell containing a magnetic stirrer bar until the intensity meter showed red laser between 80% and 90%, while blue laser was between 70% and 90%. Once stabilized, the volumetric mean diameter Dv10, Dv50 and Dv90 were measured. This laser diffraction method developed for uncoated particles was not used for spray-dried phospholipid/aspirin particles as they did not disperse well in the selected media.

2.2 Light Microscopy

Photomicrographs of the pre- and post-micronized uncoated particles were taken by dispersing them in a solution of 0.1% w/w docusate sodium in purified water USP, and using a digital imaging light microscope (Olympus BX51 with Clemex ST-2000 controller) at 400-times or 1000-times magnification. As spray-dried phospholipid/aspirin particles were found to not disperse well in the selected media, photomicrographs were taken after spreading them in the dry state over glass slides.

3. Jet Milling Trials Using Sturtevant Qualification Mill

Initial work was carried out using a Sturtevant Qualification mill with venturi #1 using nitrogen as the carrier gas. Material was fed through vibratory feeder at controlled rate and at predetermined feed and grind pressure. The effect of grinding pressure, feed rate, and second pass were studied on particle size reduction and the conditions are reported in Table 4.

TABLE 4

Jet Milling Trials using Sturtevant Qualification Mill

| | Formulation | | | |
|---|---|---|---|---|
| | 3694 | 3695 | 3701 | 3702 |
| | Milling run | | | |
| | Pass#1 | Pass#1 | Pass#1 | Pass#2 of Formulation 3695 |
| P_Feed (bar) | 7 | 7 | 7 | 7 |
| P_Grind (bar) | 3.5 | 5 | 3.5 | 5 |
| F_Flow (g/hr) | 17 | 17 | 54 | 7 |

3.1 Effect of Grind Pressure

Formulations 3694 and 3695 were compared to study effect of grind pressure on PSD (particle size distribution). Laser diffraction and microscopy results were obtained are presented in Table 5. Microscopy and laser diffraction data were found to correlate very well. When grinding pressure was increased from 3.5 to 5 bar, a measurable decrease in particle size was observed as would be expected.

TABLE 5

Effect of Grind Pressure on Aspirin Particle Size

| | Average (% RSD)/n = 3 | |
|---|---|---|
| Formulation | 3694 | 3695 |
| Dv10 (µm) | 1.9 (1.0) | 1.2 (2.2) |
| Dv50 (µm) | 3.3 (1.8) | 2.4 (1.9) |
| Dv90 (µm) | 5.9 (2.8) | 4.9 (2.6) |
| Microscopy (µm) | 1.7-5.1 | 2.0-3.5 |

3.2 Effect of Feed Rate

Formulations 3694 and 3701 were compared to study the effect of material feed rate on particle size using microscopy (Table 6). Clearly, as the flow rate was increased from 17 g/hr to 54 g/hr, significantly larger particles were obtained. This is likely the result of new material entering the milling chamber and pushing out particles to the collection bag before they undergo sufficient attrition.

TABLE 6

Effect of Feed Rate on Particle Size

| Formulation | 3694 | 3701 |
|---|---|---|
| Microscopy (µm) | 1.7-5.1 | 5.2-42.1 |

3.3 Effect of Second Milling Pass

In order to achieve the target particle size of Dv50 of 1.5 µm and Dv90 of 2 µm, formulation 3695 was passed the through mill for a second pass. Particle size analysis was carried out using laser diffraction and microscopy (Table 7). Significant particle size reduction was achieved on the second pass through the jet mill which implies that aspirin particles undergo first order size reduction, and that final particle size obtained depends upon initial particle size used.

TABLE 7

Effect of Second Milling Pass on Particle Size

| Formulation | 3695 | 3702 |
|---|---|---|
| Microscopy (µm) | 2.0-3.5 | 0.8-2.4 |

4. Jet Milling Using Sturtevant Sanitary Design Mill

In order to achieve higher feed rate with better control as well as to increase batch size, the larger 2" sanitary design mill was used according to parameters listed in Table 8. Material was processed on a second pass as well to reduce particle size to target. Formulations 3727 and 3734 were compared with 3705 and 3725 processed using the Qualification mill respectively to study reproducibility in PSD. An antistatic device was necessary to feed the powder for the second pass to minimize the effects of the static electricity imparted during the first pass.

TABLE 8

Jet Milling using Sturtevant Sanitary Design Mill

| | Mill Used | | | |
|---|---|---|---|---|
| | Q-Mill | | 2" Mill | |
| | Formulation | | | |
| | 3705 | 3725 | 3727 | 3734 |
| | Milling run | | | |
| | Pass#1 | Pass#2 (Formulation 3705) | Pass#1 | Pass#2 (Formulation 3727) |
| P_Venturi (bar) | 4.1 | 2.8 | 4.1 | 2.9 |
| P_Grind (bar) | 2.8 | 2.1 | 2.8 | 2.1 |
| F_Flow (g/hr) | 132 | 78 | 142 | 59 |
| Batch size (g) | 80 | 50 | 200 | 120 |

Aggregated particles with high static charge were obtained in all cases.

4.1 Particle Size Analysis

Figure 1:
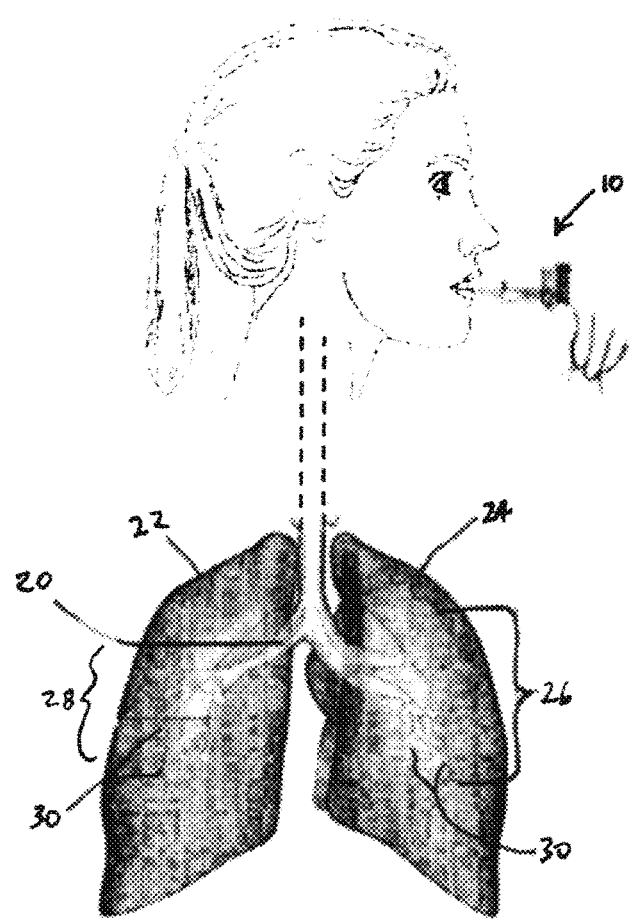
Figure 3:
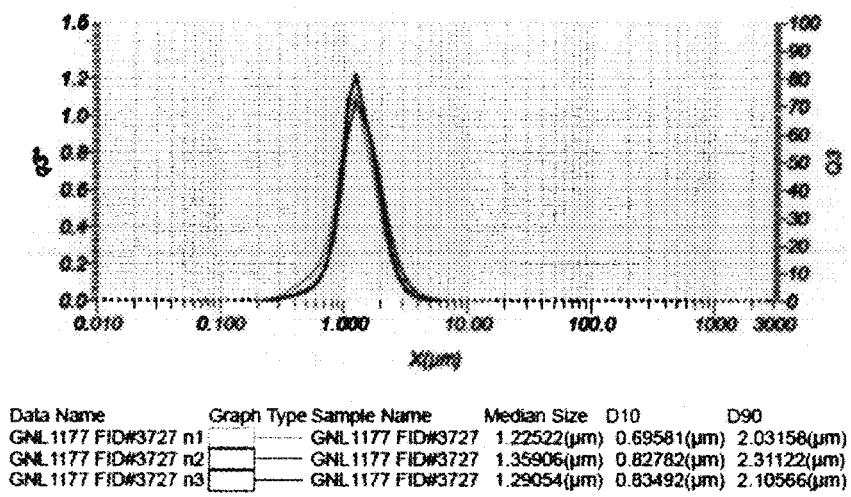
FIG. 3 shows laser diffraction data of Formulation 3727.
Figure 4:
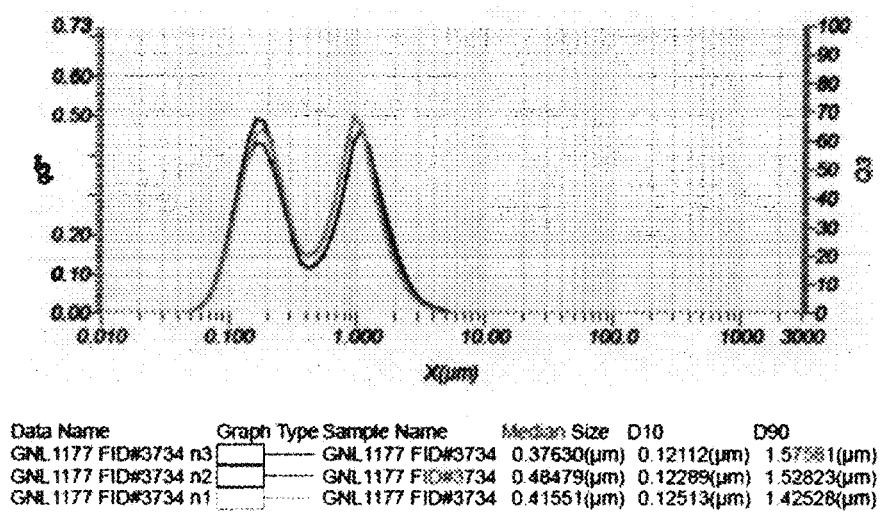
FIG. 4 shows laser diffraction data of Formulation 3734.

Particle size analysis of above formulations was carried out using laser diffraction and microscopy (Table 9, FIG. 3 and FIG. 4). Reproducible results in particle size reduction were obtained with comparable Dv10, Dv50 and Dv90 values between the two mill sizes, even with batch size increased from 80 g to 200 g for the first pass and from 50 g to 120 g for the second pass. Monomodal PSD was obtained for the first pass while a bimodal distribution was observed for the second pass.

TABLE 9

Particle Size Analysis of Jet Milled Aspirin Formulations Prepared Using Sanitary Design Mill

| | Average (% RSD)/n = 3 | | | |
|---|---|---|---|---|
| Formulation | 3705 | 3725 | 3727 | 3734 |
| Dv10 (µm) | 0.9 (5.2) | 0.1 (1.9) | 0.8 (10.0) | 0.1 (1.6) |
| Dv50 (µm) | 1.5 (3.3) | 0.4 (6.3) | 1.3 (5.2) | 0.4 (12.9) |
| Dv90 (µm) | 2.6 (4.2) | 1.8 (6.0) | 2.2 (6.7) | 1.5 (5.1) |
| Microscopy | 1.2-2.6 µm | 0.9-1.8 µm | 1.1-3.2 µm | 0.9-2.3 µm |

5. Coating

Spray-drying was used for coating. Jet milled formulation 3734, processed two passes on the 2" sanitary mill, was used further to coat with either DSPC or soy lecithin. Particles were dispersed in n-hexane containing lipid and spray-drying was selected as a method to remove solvent. In order to achieve coating around all individual particles, it was required to disperse Jet milled particles completely without settling, and therefore, continuous stirring was employed throughout the spray-drying operation.

5% w/w DSPC was used as it was found from previous work to mitigate irritation when inhaled. Additionally, soy lecithin was also used in the concentration of 0.1% w/w. As aspirin is insoluble in n-hexane, it was selected as a dispersion media for the micronized particles. Also, it has boiling point of 70° C. which is much below the melting point of aspirin (~135° C.) and therefore, an inlet temperature of 85° C. should remove solvent without affecting the aspirin particles.

A Buchi-290 spray dryer equipped with nozzle of 0.7 mm diameter was used for the study. Spray-drying was performed using nitrogen as the carrier gas with the aspirator set at 100% capacity. The flow rate of nitrogen was adjusted to 1052 L/hr (50 mm in rotameter). Before feeding the stock dispersion, feed rate was adjusted using dispersing media alone to achieve targeted outlet temperature and stabilization of the system.

5.1 Spray-Drying Using DSPC

DSPC (Lipoid PC 18:0/18:0) is an endogenous lung phospholipid with a phase transition temperature of 55° C. On heating at this temperature, DSPC transforms into a liquid crystalline phase from the gel phase, and the phospholipid layer is dispersed in n-hexane as a monolayer with a random and non-rigid structure. When jet milled aspirin particles are dispersed in the DSPC/Hexane solution, a well dispersed colloidal suspension was formed without noticeable settling. From this, it was hypothesized that spray-drying should be able to coat individual aspirin particles on solvent removal. Details of the processing are reported in Table 10.

TABLE 10

Spray-Drying Parameters for DSPC/Aspirin Formulation

| Formulation | 3739 |
|---|---|
| Suspension preparation | |
| DSPC (g) | 0.50 |
| n-hexane (g) | 490 |
| Jet milled ASA (g) | 9.50 |
| % Solid in feed | 2 |
| Suspension temperature (° C.) | 55 |
| Spray-drying parameters | |
| Inlet temperature (° C.) | 85 |
| Outlet temperature (° C.) | 56 |
| Flow rate (g/min) | 3.9 |
| Flow meter (mm) | 50 |
| Suspension temperature (° C.) | 55 |
| % Yield | 79 |

No excessive sticking to the spray-drying chamber was observed during processing and a yield of 79% was obtained. Also, the coated particles obtained were observed to be denser and less static than uncoated particles.

5.1.1 Particle Size Analysis

The spray-dried DSPC coated particles were found to not disperse as well in the 0.05% w/w soy lecithin/n-hexane solution used for particle size analysis of the uncoated aspirin particles. Some agglomeration was observed by microscopy compared to uncoated, though PSD ranges of the primary particles was collated from the microscopic images (Table 11).

TABLE 11

Particle Size of Micronized Uncoated and Spray-Dried DSPC/Aspirin Particles

| | Formulation | |
|---|---|---|
| Description | 3734 Micronized uncoated | 3739 Spray-dried DSPC/aspirin |
| Microscopy (μm) | 0.9-2.3 | 1.8-3.6 |

5.1.2 Differential Scanning Calorimetry (DSC)

A DSC study was carried out on raw aspirin, uncoated milled particles of formulation 3734 and spray-dried DSPC/aspirin particles of formulation 3739 to study any change in the crystallinity of the aspirin induced from processing.

Samples were sealed in 40 μL aluminum pans with pierced lids and analyzed using a differential scanning calorimeter (Mettler-Toledo DSC equipped with STAR® software V10.00). The samples were heated from 25° C. to 160° C. at a rate of 10° C. per minute. An empty pan served as the reference.

Figure 5:
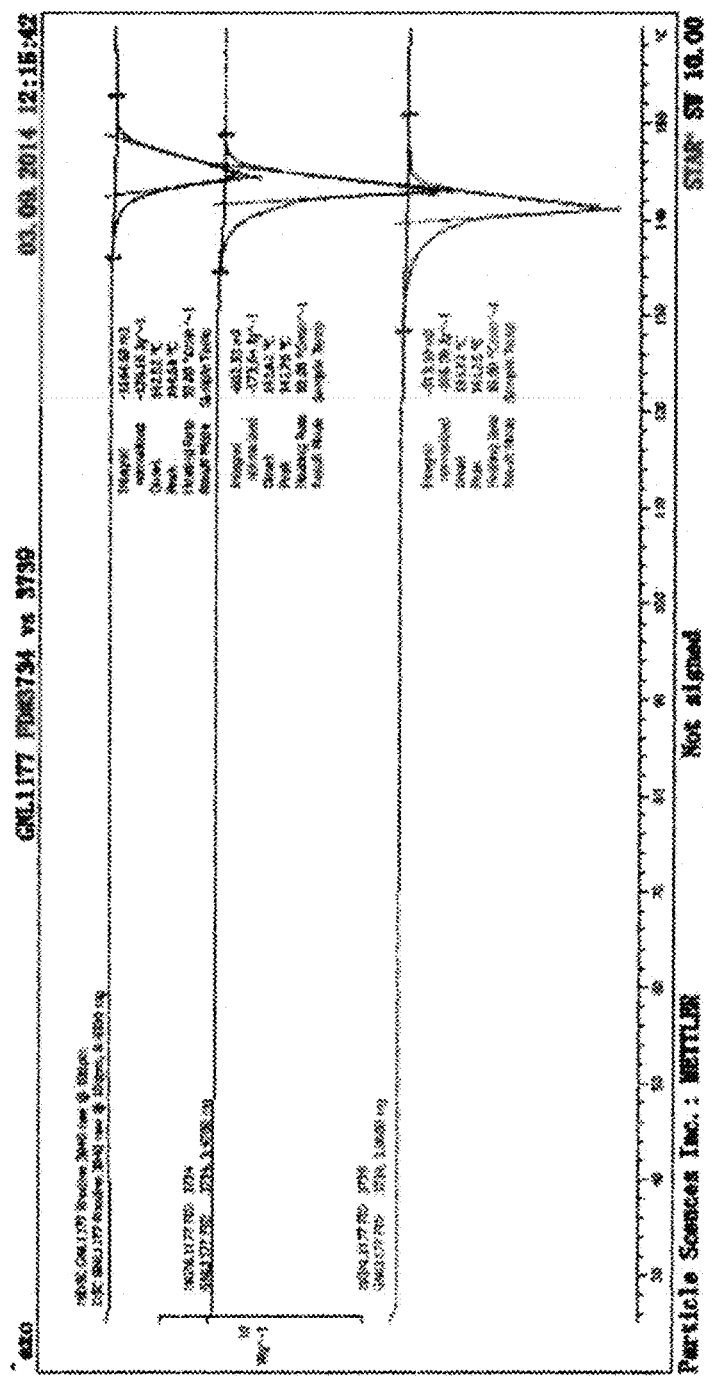
FIG. 5 shows DSC thermograms of raw, micronized uncoated and spray-dried DSPC/aspirin particles.

In all samples, a sharp endothermic peak corresponding to aspirin melting was observed. No other polymorphic conversion was observed. Also, no significant shift in peak was observed confirming no change in crystallinity of the aspirin on processing (FIG. 5, Table 12).

TABLE 12

DSC Analysis of Raw, Micronized Uncoated and Spray-Dried DSPC/Aspirin Particles

| Sample | Onset temperature (° C.) | Peak temperature (° C.) |
|---|---|---|
| Rhodine 3040 US raw | 142.5 | 144.7 |
| Micronized uncoated aspirin | 141.6 | 142.8 |
| Spray-dried DSPC/aspirin | 139.7 | 141.3 |

5.1.3 Thermogravimetric Analysis (TGA)

TGA was carried out for the micronized uncoated aspirin particles of formulation 3734 and spray-dried DSPC/aspirin particles of formulation 3739 to evaluate those for residual solvent and change in moisture content of the particles on spray-drying.

TGA of spray-dried powder carried out in 40 μL aluminum open pans by heating them from 25° C. to 160° C. at a rate of 10° C. per minute using Mettler-Toledo TGA/DSC1 equipped with STAR® software V10.00. The % weight loss was measured from 25° C. to 120° C. and compared between pre- and post-spray-drying.

Figure 6:
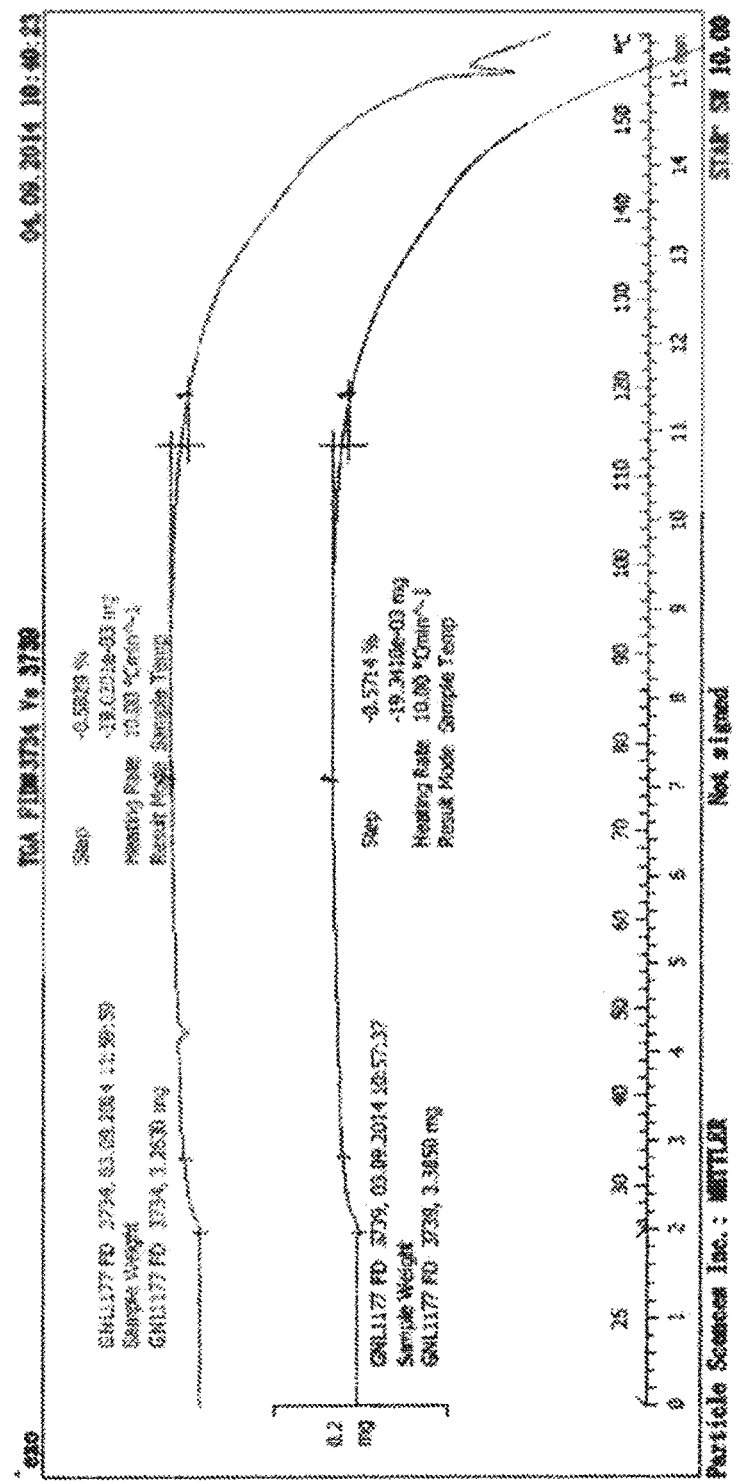
FIG. 6 shows TGA of micronized uncoated and spray-dried DSPC/aspirin particles.

TGA data suggests that there is no residual hexane in spray-dried particles, as the % weight loss before and after spray drying show similar values. The 0.57% weight loss is likely indicative of the moisture content of pre- and post-spray-dried aspirin particles (FIG. 6, Table 13).

TABLE 13

% Weight Loss for Micronized Uncoated and Spray-Dried DSPC/Aspirin Particles

| Formulation | % weight loss (g) |
|---|---|
| Micronized uncoated aspirin | 0.58 |
| Spray-dried DSPC/aspirin | 0.57 |

5.2 Spray-Drying Aspirin Particles Using Soy Lecithin

Soy lecithin was selected as an excipient as it is also approved for inhalation drug delivery and it was able to disperse jet milled aspirin particles well. Therefore, it was expected to be able to coat individual aspirin particle on solvent removal.

Soy lecithin was dissolved in n-hexane and jet milled aspirin particles dispersed in it with stirring. However, unlike the dispersion of aspirin in DSPC, the soy lecithin in 0.1% w/w concentration was not able to form colloidal dispersion, and some settling was observed. Therefore, continuous stirring of the feed suspension during spray-drying was used to maintain the dispersion of the aspirin particles. Spray-drying was carried out to remove n-hexane and coat aspirin particles using the parameters in Table 14. A 54% yield was obtained.

TABLE 14

Spray-Drying Parameters for Soy Lecithin/Aspirin Formulation

| Formulation | 3740 |
|---|---|
| Suspension preparation | |
| Soy lecithin (g) | 0.01 |
| n-hexane (g) | 490 |
| Jet milled ASA (g) | 9.99 |
| % Solid in feed | 2 |
| Suspension temperature (° C.) | RT |
| Spray-drying parameters | |
| Inlet temperature (° C.) | 85 |
| Outlet temperature (° C.) | 59 |
| Flow rate (g/min) | 3.9 |
| Flow meter (mm) | 50 |
| Suspension temperature | RT |
| Yield | 54% |

5.2.1 Particle Size Analysis

Particle size analysis was carried out using powder microscopy and compared with micronized uncoated and spray-dried DSPC/aspirin. Particle size of both spray-dried formulations suggest satisfactory results (Table 15).

TABLE 15

Particle Size Analysis of Spray-dried Soy Lecithin/Aspirin Particles

| | Formulation | | |
|---|---|---|---|
| | 3734 | 3739 | 3740 |
| | Description | | |
| | Micronized uncoated aspirin | Spray-dried DSPC/aspirin | Spray-dried soy lecithin/Aspirin |
| Microscopy (μm) | 0.9-2.3 | 1.8-3.6 | 1.7-3.3 |

Conclusions

The micronization of aspirin yielded an approximately 70 fold reduction in the starting particle size. Spray-drying with DSPC or soy lecithin resulted in satisfactory particle size for deep lung tissue drug delivery with maximum size of 3.6 μm. Spray-dried DSPC/aspirin particles were found to be less static than soy lecithin/aspirin particles, and even less static than micronized uncoated aspirin particles. The crystalline structure of aspirin did not change during milling or spray drying as observed by DSC study. DSC studies also suggested absence of any other event such as polymorph conversion during processing. No traces of residual solvent found in spray dried DSPC/aspirin during TGA analysis.

Example 2 Emitted Dose Analysis of DSPC/Aspirin Particles and Soy Lecithin/Aspirin Particles The aerodynamic particle size distributions (APSDs) of the ASA powders were determined by evaluating emitted doses gravimetrically through two DPI devices, the Twin-Caps and the RS01, using a Next Generation Impactor (NGI). Flow rates of approximately 40 and 100 L/min provided the 4 kPa pressure drop across the TwinCaps and RS01 devices, respectively, as stipulated by USP <601>, Inhalation and Nasal Drug Products: Aerosol, Sprays, and Powders—Performance Quality Tests.

The TwinCaps DPI was tested (2 actuations) using various loaded doses. Testing was performed to determine the approximate emitted dose from the device based on weight. Each test was performed using a freshly prepared NGI.

Low emitted doses were observed with the TwinCaps device, so appropriate setup of the DPI with NGI apparatus was demonstrated using the TwinCaps loaded with lactose powder (60 mg). The lactose powder gave a 94.5% emitted dose at a flow of 40 L/min.

The Plastiape RS01 monodose DPI inhaler was also tested using various loaded doses in Size 3 HPMC capsules to determine approximate emitted dose based on the weight. Table 16 summarizes the gravimetric testing results.

Because the RS01 gave a higher emitted dose than TwinCaps, the RS01 was used for subsequent collection method development.

TABLE 16

Gravimetric Testing for Device Feasibility

| Powder Type | DPI Device | Flow Rate (L/min) | Fill Weight (mg) | Total Emitted Dose (mg) | % Emitted (based on fill weight) |
|---|---|---|---|---|---|
| Aspirin (Soy Lecithin) | TwinCaps | 30 | 69.42 | 4.53 | 6.5 |
| Aspirin (Soy Lecithin) | TwinCaps | 40 | 59.88 | 13.12 | 21.9 |
| Aspirin (DSPC) | TwinCaps | 40 | 60.27 | 2.95 | 4.9 |
| Lactose | TwinCaps | 40 | 60.00 | 56.73 | 94.5 |
| Aspirin (Soy Lecithin) | RS01 | 100 | 20.11 | 15.37 | 76.4 |
| Aspirin (Soy Lecithin) | RS01 | 100 | 32.81 | 21.20 | 64.6 |
| Aspirin (DSPC) | RS01 | 100 | 29.20 | 25.15 | 86.1 |
| Aspirin (Soy Lecithin) | RS01 | 100 | 71.08 | 59.81 | 84.1 |
| Aspirin (DSPC) | RS01 | 100 | 70.09 | 62.08 | 88.6 |

Example 3 Particle Size Distribution (PSD) Analysis of Inhaled Aspirin by Dry Dispersion and Laser Diffraction Particle size analysis was carried out using laser diffraction analysis of dry dispersed spray-dried DSPC/aspirin particles of formulation 3739 (Table 17), and spray-dried soy lecithin/aspirin particles formulation 3740 (Table 18) (see Example 1 for the preparation of DSPC/aspirin particles and soy lecithin/aspirin particles).

TABLE 17

| Lens | Primary Pressure (bar) | Replicate | Particle Size (μm) | | | | | Optical Conc. |
|---|---|---|---|---|---|---|---|---|
| | | | X10 | X50 | X90 | VMD | GSD | |
| R3 | 1.0 | 1 | 0.96 | 2.29 | 4.47 | 2.56 | 1.82 | 8.71 |
| R2 | 1.0 | 1 | 0.83 | 2.31 | 4.49 | 2.56 | 1.90 | 7.56 |
| | | 2 | 0.79 | 2.24 | 4.44 | 2.49 | 1.93 | 7.10 |
| R1 | 0.7 | 1 | 0.66 | 2.63 | 5.27 | 2.88 | 2.07 | 9.21 |
| | | 2 | 0.64 | 2.59 | 5.18 | 2.84 | 2.07 | 5.72 |
| | 0.9 | 1 | 0.62 | 2.34 | 4.63 | 2.57 | 2.01 | 4.78 |
| | | 2 | 0.57 | 2.31 | 4.68 | 2.55 | 2.09 | 5.98 |
| | 1.0 | 1 | 0.58 | 2.31 | 4.69 | 2.54 | 2.11 | 10.98 |
| | | 2 | 0.60 | 2.34 | 4.69 | 2.56 | 2.08 | 6.53 |
| | | 3 | 0.56 | 2.31 | 4.76 | 2.57 | 2.14 | 6.74 |
| | | 4 | 0.57 | 2.26 | 4.51 | 2.48 | 2.07 | 7.97 |
| | | 5 | 0.58 | 2.28 | 4.53 | 2.49 | 2.06 | 8.20 |
| | 1.2 | 1 | 0.56 | 2.13 | 4.17 | 2.32 | 2.03 | 4.38 |
| | | 2 | 0.55 | 2.12 | 4.17 | 2.32 | 2.05 | 12.60 |
| | 2.0 | 1 | 0.60 | 2.03 | 4.03 | 2.54 | 1.97 | 6.03 |
| | | 2 | 0.54 | 2.03 | 4.25 | 2.57 | 2.12 | 7.63 |
| | 3.0 | 1 | 0.55 | 1.84 | 3.68 | 2.13 | 2.03 | 8.88 |
| | | 2 | 0.52 | 1.81 | 3.63 | 2.01 | 2.07 | 8.49 |
| | 4.0 | 1 | 0.47 | 1.79 | 3.64 | 2.00 | 2.12 | 6.41 |
| | | 2 | 0.52 | 1.80 | 3.58 | 2.00 | 2.03 | 7.56 |

TABLE 18

| Lens | Primary Pressure (bar) | Replicate | Particle Size (μm) | | | | | Optical Conc. |
|---|---|---|---|---|---|---|---|---|
| | | | X10 | X50 | X90 | VMD | GSD | |
| R1 | 1.0 | 1 | 0.50 | 1.91 | 3.90 | 2.12 | 2.11 | 11.28 |
| | | 2 | 0.50 | 1.89 | 3.73 | 2.07 | 2.03 | 3.89 |
| | | 3 | 0.49 | 1.91 | 3.83 | 2.11 | 2.09 | 9.58 |
| | | 4 | 0.52 | 1.90 | 3.66 | 2.06 | 2.00 | 4.70 |
| | | 5 | 0.49 | 1.90 | 3.83 | 2.10 | 2.08 | 6.84 |
| | | Average | 0.50 | 1.90 | 3.79 | 2.09 | 2.06 | |
| | | % RSD | 2 | 0 | 2 | 1 | 2 | |

RSD: relative standard deviation.

Example 4 NGI (Next-Generation Impactor) Analysis of Spray Dried Aspirin/DSPC Particles The dry powders of Example 1 were evaluated for aerodynamic performance. APSD via NGI was determined (n=5) for ASA-5% DSPC using #3 HPMC capsules filled with 37±1 mg of powder. Two of the replicates were performed by delivering two capsules of powder to the cascade impactor. Three of the replicates were performed by delivering one capsule of powder. The DPI device used was a monodose inhaler. The NGI test conditions ranged between 20° C. and 25° C., and between 40% and 50% RH (relative humidity) (Table 19).

TABLE 19

| | NGI 1 | NGI 2 | NGI 3 | NGI 4 | NGI 5 |
|---|---|---|---|---|---|
| Controlled condition | 21.83 C./ 46.7% RH | 22.66 C./ 47.3% RH | 21.93 C./ 46.9% RH | 21.93 C./ 46.9% RH | 21.99 C./ 43.1% RH |
| Measured | 99.1 | 98.4 | 97.6 | 100.0 | 100.5 |
| Flow | SLPM | SLPM | SLPM | SLPM | SLPM |

Table 20 shows the aerodynamic properties of DSPC/aspirin particles.

TABLE 20

| | 2 capsules | | 1 capsule | | |
|---|---|---|---|---|---|
| | NGI 1 | NGI 2 | NGI 3 | NGI 4 | NGI 5 |
| Device, μg | 7876.4 | 9010.6 | 4267.0 | 4118.0 | 5115.8 |
| Capsule 1, μg | 653.6 | 717.9 | 484.6 | 464.5 | 670.5 |
| Capsule 2, μg | 616.2 | 560.3 | NA | NA | NA |
| Induction Port, μg | 11611.6 | 14550.8 | 7253.0 | 7454.4 | 6792.6 |
| Stage 1, μg | 10232.0 | 9393.6 | 3704.8 | 4257.6 | 5481.2 |
| Stage 2, μg | 17402.0 | 16198.0 | 8284.4 | 8136.4 | 8758.4 |
| Stage 3, μg | 10882.4 | 9993.6 | 5600.8 | 4976.4 | 5087.6 |
| Stage 4, μg | 4884.0 | 4864.4 | 2791.2 | 2387.2 | 2273.6 |
| Stage 5, μg | 1670.0 | 1514.8 | 983.2 | 757.6 | 891.2 |
| Stage 6, μg | 983.8 | 1076.6 | 619.8 | 471.9 | 530.3 |
| Stage 7, μg | 575.6 | 498.2 | 318.9 | 262.9 | 284.1 |
| MOC, μg | 320.8 | 292.4 | 134.0 | 158.0 | 201.7 |
| Nozzles, μg | 5364.8 | 6363.2 | 2546.4 | 2833.6 | 3280.8 |
| Nominal loaded mass (mg) | 74 | 74 | 37 | 37 | 37 |
| ED (mg) | 63.93 | 64.75 | 32.24 | 31.70 | 33.58 |
| Nominal % ED (mg) | 86% | 88% | 87% | 86% | 91% |
| FPD (mg) | 32.2 | 30.8 | 16.6 | 15.1 | 16.0 |
| FPF (%) | 50.4 | 47.5 | 51.5 | 47.7 | 47.5 |
| MMAD (μm) | 3.94 | 3.93 | 3.62 | 3.91 | 4.12 |
| GSD | 1.91 | 1.94 | 1.91 | 1.94 | 2.00 |
| Recovery (%) | 99.8 | 100.0 | 101.2 | 100.1 | 103.7 |

Example 5 NGI Analysis of Spray Dried Aspirin/Soy Lecithin Particles

The dry powders of Example 1 were evaluated for aerodynamic performance. The DPI device used was a monodose inhaler. APSD via NGI was determined (n=5) for ASA-0.1% soy lecithin using #3 HPMC capsules filled with 37±1 mg of powder. Because of concerns that the powder load (approx. 74 mg) for delivery of two capsules may overload the NGI, testing was performed with both one and two capsules delivery regimens. Two of the replicates were performed by delivering two capsules of powder to the cascade impactor. Three of the replicates were performed by delivering one capsule of powder. The NGI test conditions ranged between 20° C. and 25° C., and between 40% and 50% RH (relative humidity) (Table 21).

TABLE 21

| | NGI 1 | NGI 2 | NGI 3 | NGI 4 | NGI 5 |
|---|---|---|---|---|---|
| Controlled condition | 22.57 C./ 49.6% RH | 22.16 C./ 48.7% RH | 22.14 C./ 47.9% RH | 21.76 C./ 45.1% RH | 21.66 C./ 45.1% RH |
| Measured | 98.7 | 97.6 | 99.0 | 100.0 | 97.5 |
| Flow | SLPM | SLPM | SLPM | SLPM | SLPM |

Table 22 shows the aerodynamic properties of soy lecithin/aspirin particles.

TABLE 22

| | 2 capsules | | 1 capsule | | |
|---|---|---|---|---|---|
| | NGI 1 | NGI 2 | NGI 3 | NGI 4 | NGI 5 |
| Device, μg | 13139.2 | 15032.8 | 7664.0 | 6554.6 | 8382.0 |
| Capsule 1, μg | 1259.1 | 1607.1 | 1595.1 | 1078.2 | 916.0 |

TABLE 22-continued

|  | 2 capsules | | 1 capsule | | |
| --- | --- | --- | --- | --- | --- |
|  | NGI 1 | NGI 2 | NGI 3 | NGI 4 | NGI 5 |
| Capsule 2, µg | 2893.7 | 1050.2 | NA | NA | NA |
| Induction Port, µg | 5834.4 | 5586.6 | 3008.0 | 3604.4 | 3795.8 |
| Stage 1, µg | 4378.4 | 5104.0 | 1962.0 | 2274.8 | 2266.0 |
| Stage 2, µg | 12060.0 | 12890.8 | 5726.0 | 6028.0 | 6028.0 |
| Stage 3, µg | 15818.4 | 16041.6 | 7544.0 | 7687.2 | 7712.0 |
| Stage 4, µg | 11276.8 | 11301.6 | 5556.8 | 5345.6 | 5485.6 |
| Stage 5, µg | 3305.2 | 3182.0 | 1692.4 | 1622.4 | 1694.4 |
| Stage 6, µg | 1272.6 | 1161.2 | 749.5 | 728.2 | 658.7 |
| Stage 7, µg | 708.4 | 605.2 | 436.4 | 414.9 | 366.2 |
| MOC, µg | 340.8 | 375.8 | 231.8 | 228.6 | 236.9 |
| Nozzles, µg | 4105.6 | 4928.0 | 1812.8 | 2306.4 | 2121.6 |
| Nominal loaded mass (mg) | 74 | 74 | 37 | 37 | 37 |
| ED (mg) | 59.10 | 61.18 | 28.72 | 30.24 | 30.37 |
| Nominal % ED (mg) | 80% | 83% | 78% | 82% | 82% |
| FPD (mg) | 42.7 | 43.7 | 20.9 | 21.2 | 21.2 |
| FPF (%) | 72.3 | 71.5 | 72.7 | 70.0 | 69.7 |
| MMAD (µm) | 2.71 | 2.79 | 2.65 | 2.72 | 2.72 |
| GSD | 1.72 | 1.73 | 1.75 | 1.75 | 1.75 |
| Recovery (%) | 104.6 | 104.0 | 104.4 | 103.1 | 104.5 |

Example 6 HPLC Analysis of Aspirin

The following method analyzed delivered dose and NGI samples using general parameters from USP methodology. The method was designed to accurately assay the amount of aspirin in a given sample over a range suitable for NGI collections. Methodology was specifically tailored to the two spray dried drug products—95:5 Aspirin:DSPC and 99.9:0.1 Aspirin: Soy Lecithin.

Equipment

The HPLC column was Phenomenex Luna C18(2) 5 µm, 4.6×100 mm. Shimadzu HPLC Equipment was used, including Shimadzu SIL-HTC Autosampler, Shimadzu CTO-10ASVP Column Oven, Shimadzu LC-10ADVP Binary HPLC Pump, Shimadzu DGU-14A Inline Degasser, Shimadzu UV Detector, and Computer with Shimadzu Class VP software.

Materials

Mobile Phase A was 69:28:3 Water:Methanol:Glacial Acetic Acid. Mobile Phase B was 97:3 Methanol:Glacial Acetic Acid. Diluent was 95:5 Methanol:Glacial Acetic Acid. Needlewash was 50:50 Water:Methanol. The working standard was 750 µg/mL aspirin (working standard A "WSA" and working standard B "WSB").

HPLC Conditions and Analysis

Flow rate was 2.0 mL/min. The sample injection volume was 10 µL. The gradient was run according to the timing scheme in Table 23.

TABLE 23

| HPLC Gradient Program | |
| --- | --- |
| Time (min) | % B |
| 0.00 | 0.0 |
| 3.80 | 0.0 |
| 3.81 | 100.0 |
| 5.80 | 100.0 |
| 5.81 | 0.0 |
| 8.00 | STOP |

The analysis of the samples was in the following sequence:

| A. Blank | (2 injections) |
| --- | --- |
| B. Working Standard A | (6 injections) |
| C. Working Standard B | (2 injections) |
| D. Blank | (1 injection) |
| E. Sample | (1 injection each) |
| F. WSB (QC Standard) | (1 injection) |

Repeat steps E-F as necessary ensuring that the last injection of a sequence is a QC standard.

The standard agreement between WSA and WSB must be within 97.0-103.0%. The QC standard agreement between the ongoing standard analysis and initial analysis (n=2) for WSB must between 97.0-103.0%.

The standard agreement between WSA and WSB was calculated according to the equation below.

$$SA = \frac{A_{WSA}}{A_{WSB}} \times \frac{C_{WSB}}{C_{WSA}} \times 100$$

Where:
SA=Standard Agreement (%)
$A_{WSA}$=WSA Average Area (n=6)
$A_{WSB}$=WSB Average Area (n=2)
$C_{WSA}$=WSA Theoretical Concentration (µg/mL)
$C_{WSB}$=WSB Theoretical Concentration (µg/mL)
100=Conversion to %

The % recovery of the QC standard(s) was calculated according to the equation below.

$$QC = \frac{A_{QC}}{A_{WSB}} \times 100$$

Where:
QC=QC % Recovery
$A_{QC}$=QC Area
$A_{WSB}$=Initial WSB Average Area (n=2)
100=Conversion to %

The concentration of samples was calculated according to the equation below.

$$C_{SX} = \frac{A_{SX}}{A_{WSA}} \times C_{WSA}$$

Where:
$C_{SX}$=Sample Concentration (µg/mL)
$A_{SX}$=Sample Area
$A_{WSA}$=WSA Average Area (n=6) Area
$C_{WSA}$=Theoretical WSA Concentration (µg/mL)

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neutral gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

It is to be understood that, while the subject technology has been described in conjunction with the detailed description, thereof, the foregoing description is intended to illustrate and not limit the scope of the subject technology. Other aspects, advantages, and modifications of the subject technology are within the scope of the claims set forth below. The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

What is claimed is:

1. A dry powder composition for delivery to a subjects lungs by a dry powder inhaler, the composition comprising dry particles that comprise acetylsalicylic acid, or a pharmaceutically acceptable salt thereof; wherein said dry particles have a mass median aerodynamic diameter (MMAD) within a range of 0.5 µm to 5 µm, wherein said dry particles have a DV50 in a range of 3-6.7 µm and a DV10 in a range of 0.9-3.3 µm wherein the dry particles further comprise a pharmaceutically acceptable excipient, wherein the pharmaceutically acceptable excipient comprises one or more phospholipids in an amount ranging from 0.1% (w/w) to 10% (w/w) of the composition, wherein acetylsalicylic acid, or a pharmaceutically acceptable salt thereof, is in an amount of 50% (w/w) or more of the composition, and wherein the dry powder composition is free of carrier particles.

2. The dry powder composition of claim 1, wherein the dry particles have an MMAD size distribution such that said particles exhibit a DV90 less than 20 µm a DV 50 less than 4 µm, and a DV10 less than 2 µm.

3. The dry powder composition of claim 1, wherein the composition comprises particles have an MMAD size distribution such that said particles exhibit a DV90 less than 10 µm, a DV50 less than 4 µm, and a DV10 less than 1 µm.

4. The dry powder composition of claim 1, wherein the particles have an MMAD size distribution such that said particles exhibit a DV90 less than 6 µm.

5. The dry powder composition of claim 1, wherein the phospholipid is dipalmitoyl phosphotidylcholine (DPPC), distearoyl phosphotidylcholine (DSPC), lecithin, or a combination thereof.

6. The dry powder composition of claim 1, wherein the phospholipid is in an amount ranging from 1% to 5% w/w of the composition.

7. The dry powder composition of claim 1, further comprising clopidogrel.

8. A drug delivery system effective to reduce the risk of a thromboembolic event or treat thrombosis, wherein the system comprises the dry powder composition of claim 1, and wherein the acetylsalicylic acid, or a pharmaceutically acceptable salt thereof, is present at a dose of 40 mg or less.

9. A method of treating thrombosis or reducing the risk of a thromboembolic event, comprising administering to a subject in need thereof the dry powder composition of claim 1 by a dry powder inhaler, wherein the dose of the acetylsalicylic acid administered to said subject is 40 mg or less.

10. The method of claim 9, wherein the dry powder composition comprises acetylsalicylic acid and clopidogrel, and wherein the dose of the clopidogrel administered to the subject is 75 mg or less.

11. The dry powder composition of claim 1, wherein acetylsalicylic acid, or a pharmaceutically acceptable salt thereof, is in an amount of 60% (w/w) or more of the composition.

12. The dry powder composition of claim 1, wherein acetylsalicylic acid, or a pharmaceutically acceptable salt thereof, is in an amount of 70% (w/w) or more of the composition.

13. The dry powder composition of claim 1, wherein acetylsalicylic acid, or a pharmaceutically acceptable salt thereof, is in an amount of 80% (w/w) or more of the composition.

14. The dry powder composition of claim 1, wherein acetylsalicylic acid, or a pharmaceutically acceptable salt thereof, is in an amount of 90% (w/w) or more of the composition.

* * * * *